US011007092B2

(12) United States Patent
Sauer et al.

(10) Patent No.: US 11,007,092 B2
(45) Date of Patent: May 18, 2021

(54) APPARATUSES AND METHODS FOR MAKING ABSORBENT ARTICLES WITH LOW INTENSITY SIDE SEAM REGIONS

(71) Applicant: The Procter & Gamble Company, Cincinnati, OH (US)

(72) Inventors: Linda Ann Sauer, Colerain Township, OH (US); Ronald Joseph Zink, II, Blue Ash, OH (US); Jason Ashley Wagner, Lawrenceburg, IN (US)

(73) Assignee: The Procter & Gamble Company, Cincinnati, OH (US)

( * ) Notice: Subject to any disclaimer, the term of this patent is extended or adjusted under 35 U.S.C. 154(b) by 854 days.

(21) Appl. No.: 14/967,434

(22) Filed: Dec. 14, 2015

(65) Prior Publication Data

US 2016/0175167 A1 Jun. 23, 2016

Related U.S. Application Data

(60) Provisional application No. 62/093,604, filed on Dec. 18, 2014.

(51) Int. Cl.
*A61F 13/49* (2006.01)
*A61F 13/514* (2006.01)
(Continued)

(52) U.S. Cl.
CPC .. *A61F 13/49011* (2013.01); *A61F 13/15203* (2013.01); *A61F 13/15723* (2013.01);
(Continued)

(58) Field of Classification Search
CPC .......... A61F 13/15804; A61F 13/51496; A61F 2013/15243; A61F 2013/8497
See application file for complete search history.

(56) References Cited

U.S. PATENT DOCUMENTS 3,860,003 A 1/1975 Buell
4,610,678 A 9/1986 Weisman et al.
(Continued)

FOREIGN PATENT DOCUMENTS

EP 1 712 212 A2 10/2006
JP 2008183332 8/2008
(Continued)

OTHER PUBLICATIONS

U.S. Appl. No. 14/967,421, filed Dec. 14, 2015, Zink, II.
(Continued)

*Primary Examiner* — Kathryn E Ditmer
(74) *Attorney, Agent, or Firm* — Charles R. Matson

(57) ABSTRACT

The present disclosure relates to absorbent articles and methods for assembling absorbent articles with substrates and/or components that include graphics with zones of relatively high print densities and zones of relatively low print densities. In turn, the zones of relatively low print densities may be positioned in regions that are subject to various manufacturing transformations during the assembly process. As such, the graphics may be positioned and/or printed in such a manner so as to reduce noticeable visible results of imprecise and/or inconsistent manufacturing operations performed in areas where the graphics are located.

17 Claims, 21 Drawing Sheets

(51) Int. Cl.
*A61F 13/15* (2006.01)
*A61F 13/84* (2006.01)

(52) U.S. Cl.
CPC .. *A61F 13/15731* (2013.01); *A61F 13/15747* (2013.01); *A61F 13/15804* (2013.01); *A61F 13/51496* (2013.01); *A61F 2013/15243* (2013.01); *A61F 2013/8497* (2013.01)

(56) References Cited

U.S. PATENT DOCUMENTS

| | | | |
|---|---|---|---|
| 4,673,402 A | 6/1987 | Weisman et al. | |
| 4,695,278 A | 9/1987 | Lawson | |
| 4,704,115 A | 11/1987 | Buell | |
| 4,720,321 A | 1/1988 | Smith | |
| 4,795,454 A | 1/1989 | Dragoo | |
| 4,834,735 A | 5/1989 | Alemany et al. | |
| 4,888,231 A | 12/1989 | Angstadt | |
| 4,909,803 A | 3/1990 | Aziz et al. | |
| 5,373,761 A | 12/1994 | Brining | |
| 5,562,646 A | 10/1996 | Goldman et al. | |
| 5,599,335 A | 2/1997 | Goldman et al. | |
| 5,628,097 A | 5/1997 | Benson et al. | |
| 5,669,894 A | 9/1997 | Goldman et al. | |
| 5,693,165 A | 12/1997 | Schmitz | |
| 5,916,661 A | 6/1999 | Benson et al. | |
| 6,107,539 A | 8/2000 | Palumbo et al. | |
| 6,349,867 B1 | 2/2002 | Fernfors | |
| 6,545,197 B1 | 4/2003 | Muller et al. | |
| 6,596,108 B2 | 7/2003 | McCabe | |
| 6,620,276 B1 | 9/2003 | Kuntze et al. | |
| 6,790,798 B1 | 9/2004 | Suzuki et al. | |
| 7,569,039 B2 | 8/2009 | Matsuda et al. | |
| 7,587,966 B2 | 9/2009 | Nakakado et al. | |
| 7,896,858 B2 | 3/2011 | Trennepohl et al. | |
| D657,454 S | 4/2012 | Gehrke et al. | |
| 8,377,249 B2 | 2/2013 | Gill | |
| 8,440,043 B1 | 5/2013 | Schneider et al. | |
| 8,585,666 B2 | 11/2013 | Weisman et al. | |
| 8,691,041 B2 | 4/2014 | Oetjen | |
| 8,776,683 B2 | 7/2014 | Schneider | |
| 2003/0066594 A1 | 4/2003 | Malakouti et al. | |
| 2003/0073966 A1 | 4/2003 | Sosalla et al. | |
| 2003/0158532 A1 | 8/2003 | Magee et al. | |
| 2004/0097895 A1 | 5/2004 | Busam et al. | |
| 2004/0108043 A1* | 6/2004 | Otsubo | A61F 13/15699 156/160 |
| 2004/0158212 A1 | 8/2004 | Ponomarenko et al. | |
| 2004/0243083 A1 | 12/2004 | Matsuda et al. | |
| 2005/0107764 A1 | 5/2005 | Matsuda et al. | |
| 2005/0217791 A1 | 10/2005 | Colstello et al. | |
| 2005/0267431 A1* | 12/2005 | Sasaki | A61F 13/49011 604/385.3 |
| 2006/0108054 A1* | 5/2006 | Ukegawa | A61F 13/15699 156/160 |
| 2008/0091162 A1 | 4/2008 | Maldonado et al. | |
| 2008/0132872 A1 | 6/2008 | Trennepohl et al. | |
| 2009/0030389 A1 | 1/2009 | Ashton et al. | |
| 2009/0312730 A1 | 12/2009 | LaVon et al. | |
| 2010/0168703 A1* | 7/2010 | Tange | A61F 13/496 604/365 |
| 2011/0088828 A1 | 4/2011 | Misek et al. | |
| 2011/0094661 A1 | 4/2011 | Thorson | |
| 2011/0094669 A1 | 4/2011 | Oetjen | |
| 2011/0209334 A1 | 9/2011 | Trennepohl et al. | |
| 2012/0029454 A1 | 2/2012 | Li et al. | |
| 2012/0061015 A1 | 3/2012 | LaVon et al. | |
| 2012/0061016 A1 | 3/2012 | LaVon et al. | |
| 2013/0255861 A1 | 10/2013 | Schneider | |
| 2013/0255862 A1* | 10/2013 | Schneider | A61F 13/15593 156/161 |
| 2013/0255863 A1 | 10/2013 | LaVon et al. | |
| 2013/0255864 A1 | 10/2013 | Schneider et al. | |
| 2013/0255865 A1 | 10/2013 | Brown et al. | |
| 2013/0261589 A1 | 10/2013 | Fujkawa et al. | |
| 2013/0270065 A1 | 10/2013 | Papsdorf et al. | |
| 2013/0270066 A1 | 10/2013 | Papsdorf et al. | |
| 2013/0270067 A1 | 10/2013 | Papsdorf et al. | |
| 2013/0270069 A1 | 10/2013 | Papsdorf et al. | |
| 2013/0310798 A1 | 11/2013 | Glahn et al. | |
| 2014/0005020 A1* | 1/2014 | LaVon | A61F 13/56 493/357 |
| 2014/0174648 A1 | 6/2014 | Oetjen | |
| 2014/0174651 A1 | 6/2014 | Oetjen | |
| 2015/0148768 A1 | 5/2015 | Fukasawa et al. | |
| 2016/0175161 A1 | 6/2016 | Zink, II et al. | |
| 2016/0175165 A1 | 6/2016 | Schneider et al. | |
| 2016/0175166 A1 | 6/2016 | Zink, II et al. | |
| 2016/0175168 A1 | 6/2016 | Zink, II et al. | |
| 2017/0172809 A1 | 6/2017 | Wagner et al. | |
| 2017/0172814 A1 | 6/2017 | Wagner et al. | |
| 2017/0172815 A1 | 6/2017 | Wagner et al. | |
| 2017/0172816 A1 | 6/2017 | Wagner et al. | |

FOREIGN PATENT DOCUMENTS

| | | |
|---|---|---|
| WO | WO 2015/134459 A1 | 9/2005 |
| WO | WO 2008/070131 A2 | 6/2008 |
| WO | WO 2012/054662 A1 | 4/2012 |
| WO | WO 2016/100246 A1 | 6/2016 |
| WO | WO 2016/100247 A1 | 6/2016 |
| WO | WO 2016/100501 A1 | 6/2016 |
| WO | WO 2016100250 | 6/2016 |

OTHER PUBLICATIONS

U.S. Appl. No. 14/967,430, filed Dec. 14, 2015, Zink, II.
U.S. Appl. No. 14/967,440, filed Dec. 14, 2015, Zink, II.
U.S. Appl. No. 14/967,447, filed Dec. 14, 2015, Schneider.
PCT International Search Report dated Mar. 24, 2016, 10 pages.
All Office Actions, U.S. Appl. No. 14/967,421.
All Office Actions, U.S. Appl. No. 14/967,430.
All Office Actions, U.S. Appl. No. 14/967,440.
All Office Actions, U.S. Appl. No. 14/967,447.
All Office Actions, U.S. Appl. No. 15/378,129.
All Office Actions, U.S. Appl. No. 15/378,149.
All Office Actions, U.S. Appl. No. 15/378,164.
All Office Actions, U.S. Appl. No. 15/378,195.
P&G 13655C, All Office Actions, U.S. Appl. No. 16/691,753.

* cited by examiner

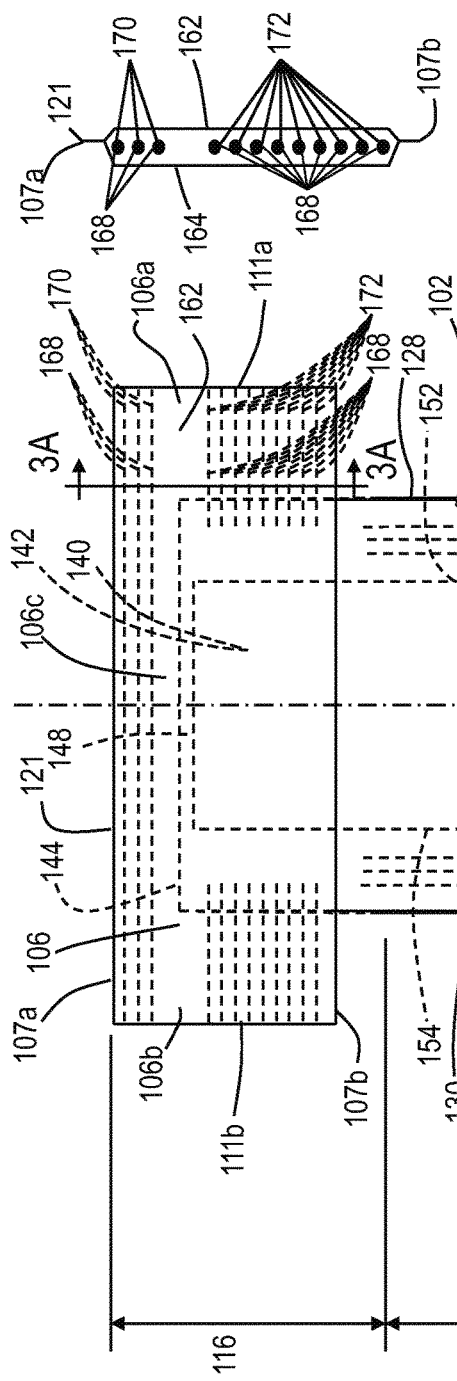
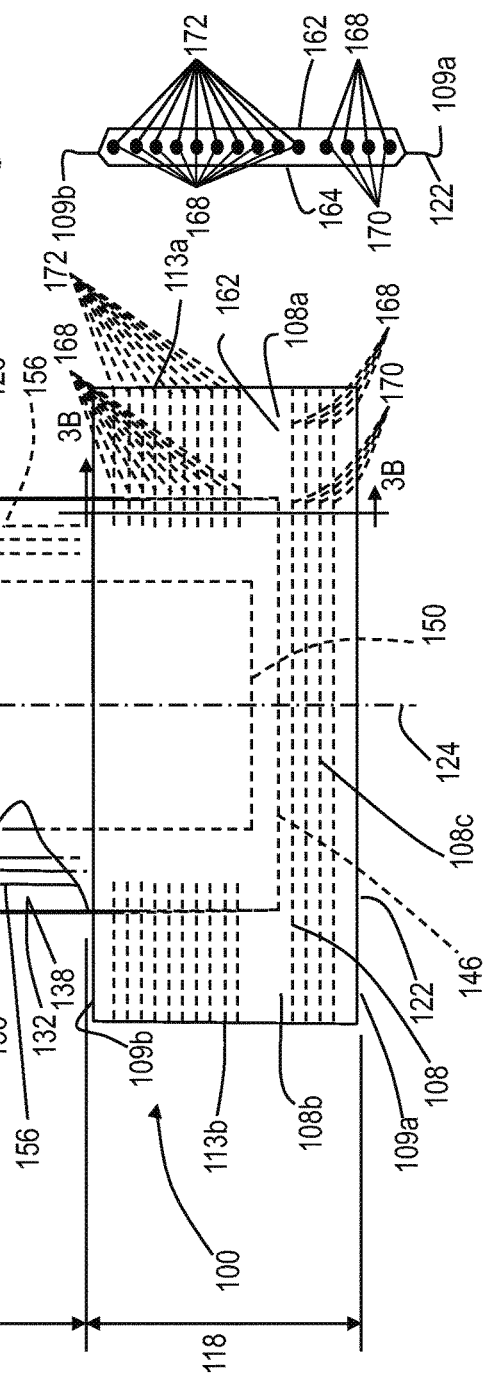

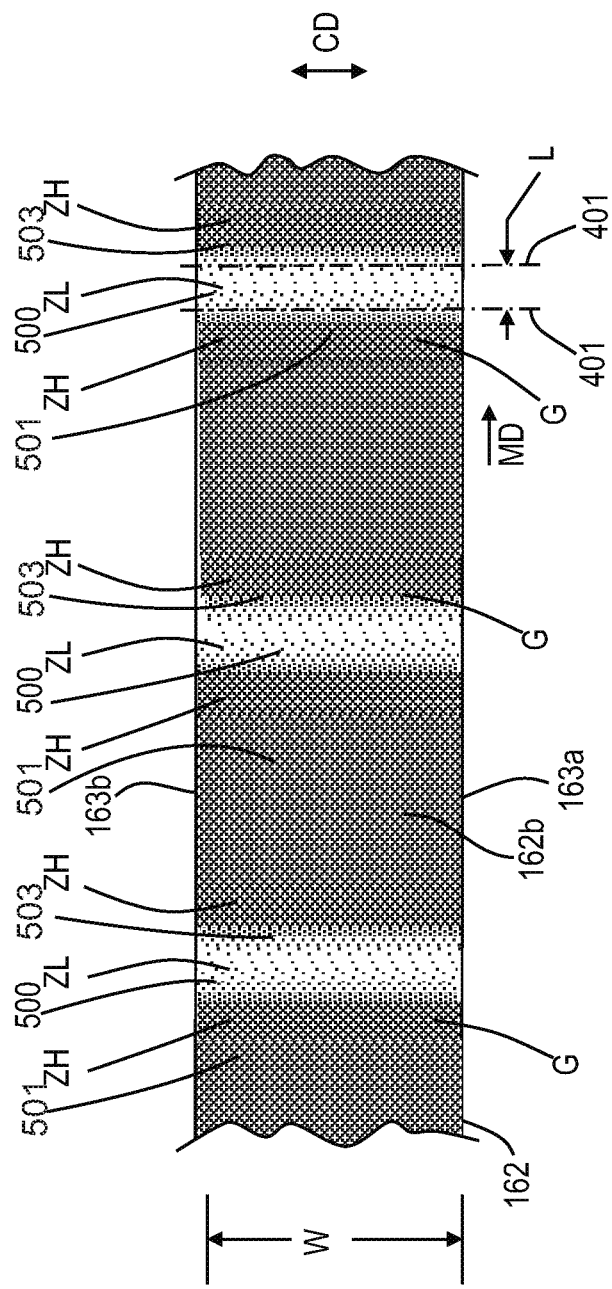
Figure 5A1

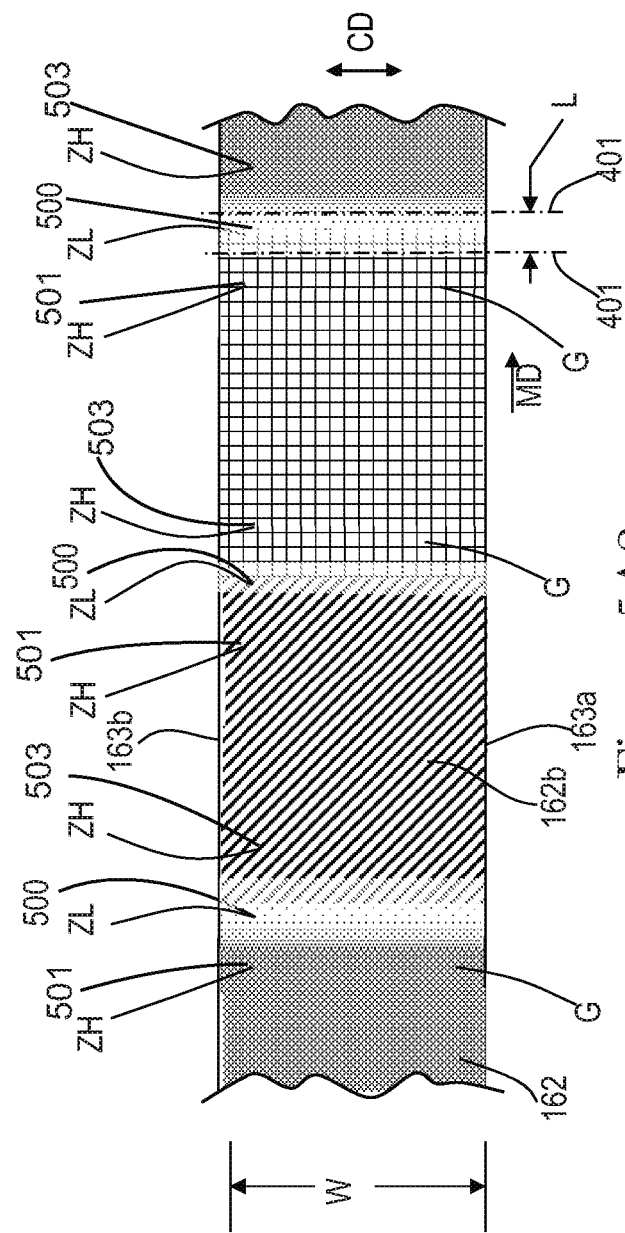
Figure 5A2

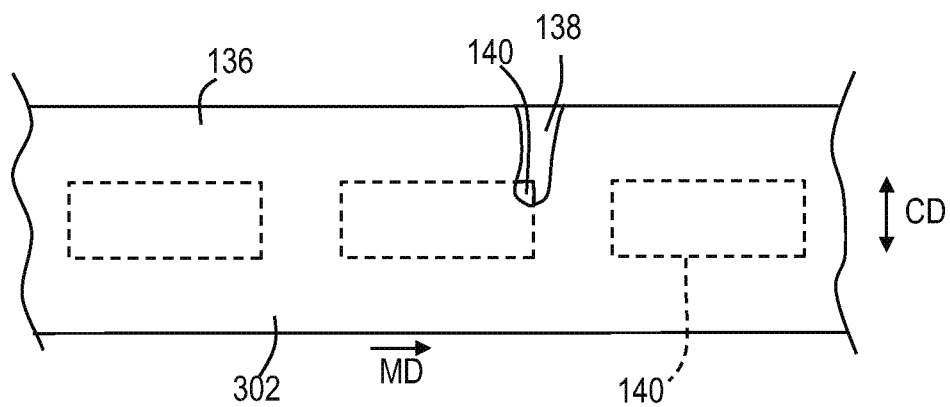
Figure 5C
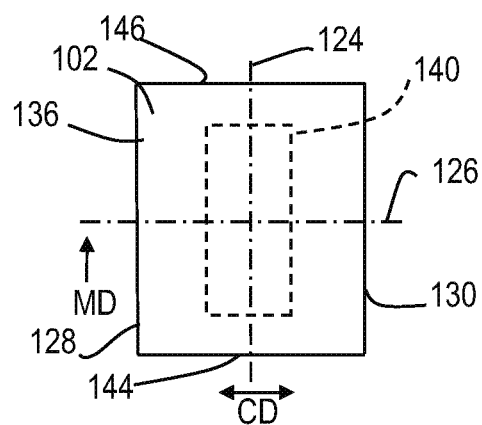
Figure 5D1
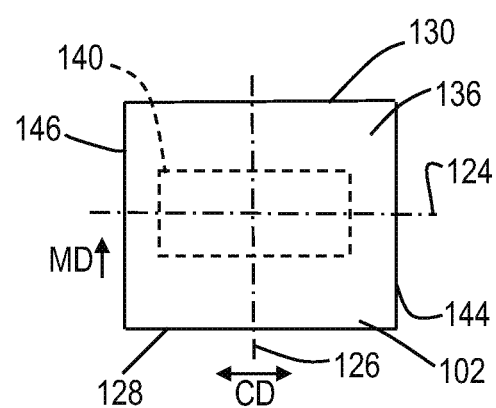
Figure 5D2

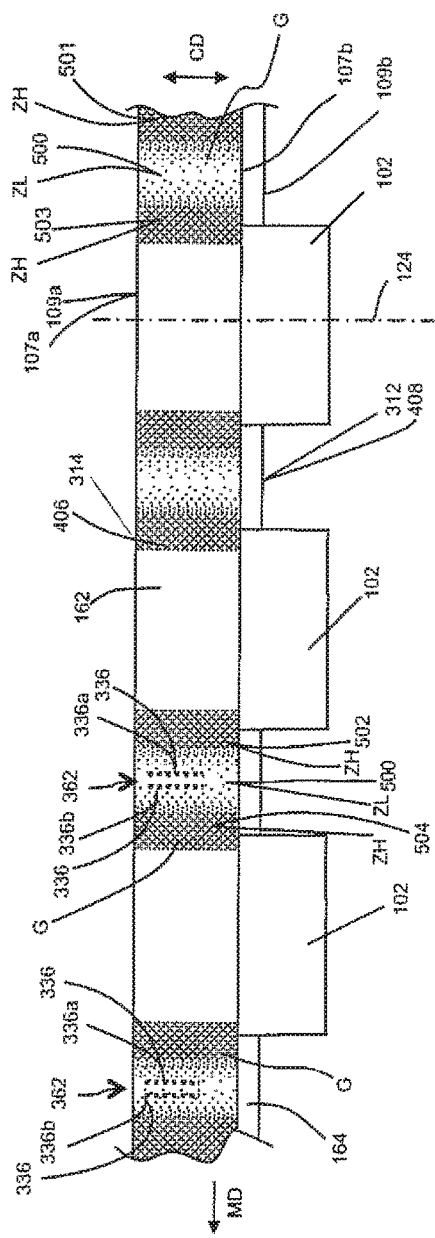
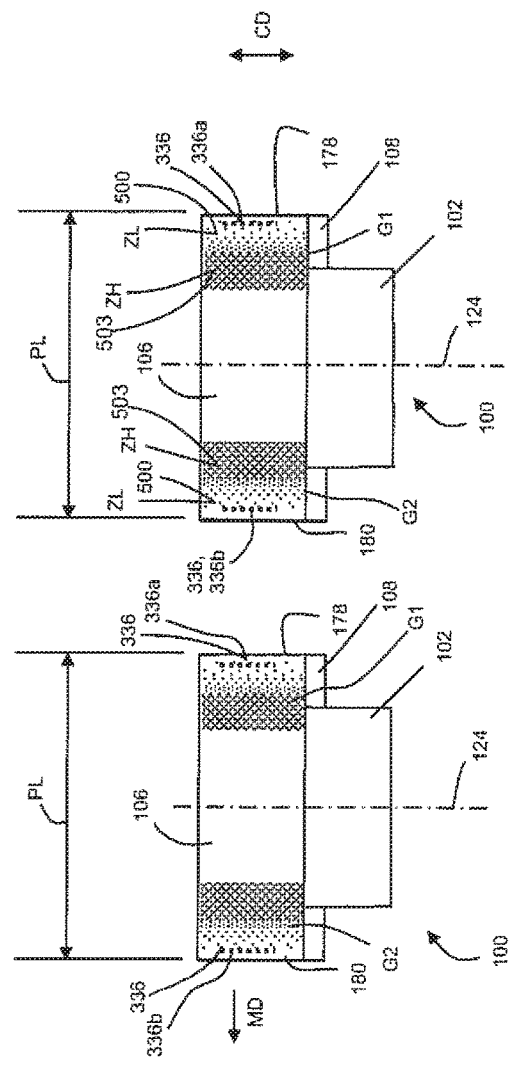
Figure 5F
Figure 5G

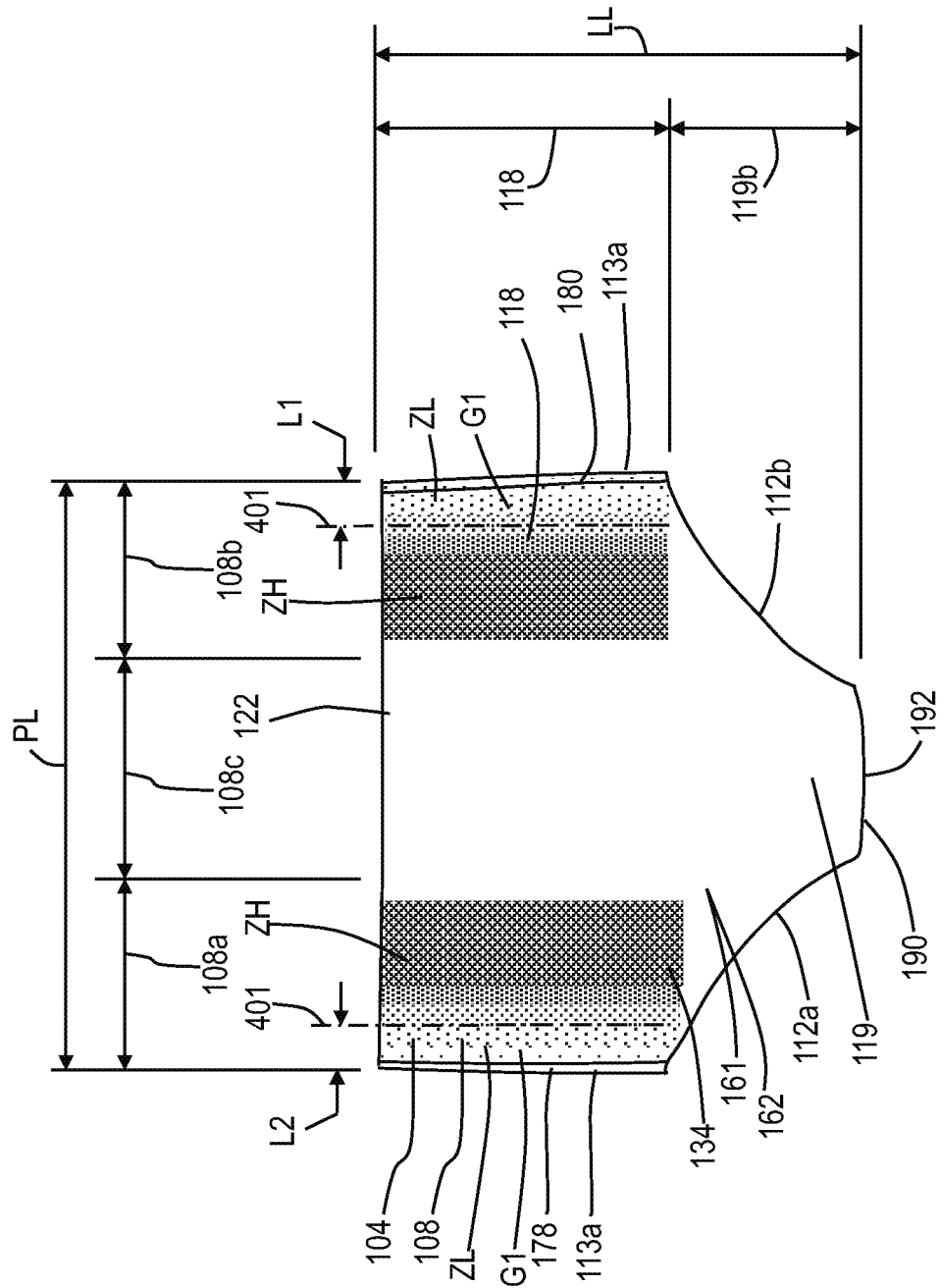

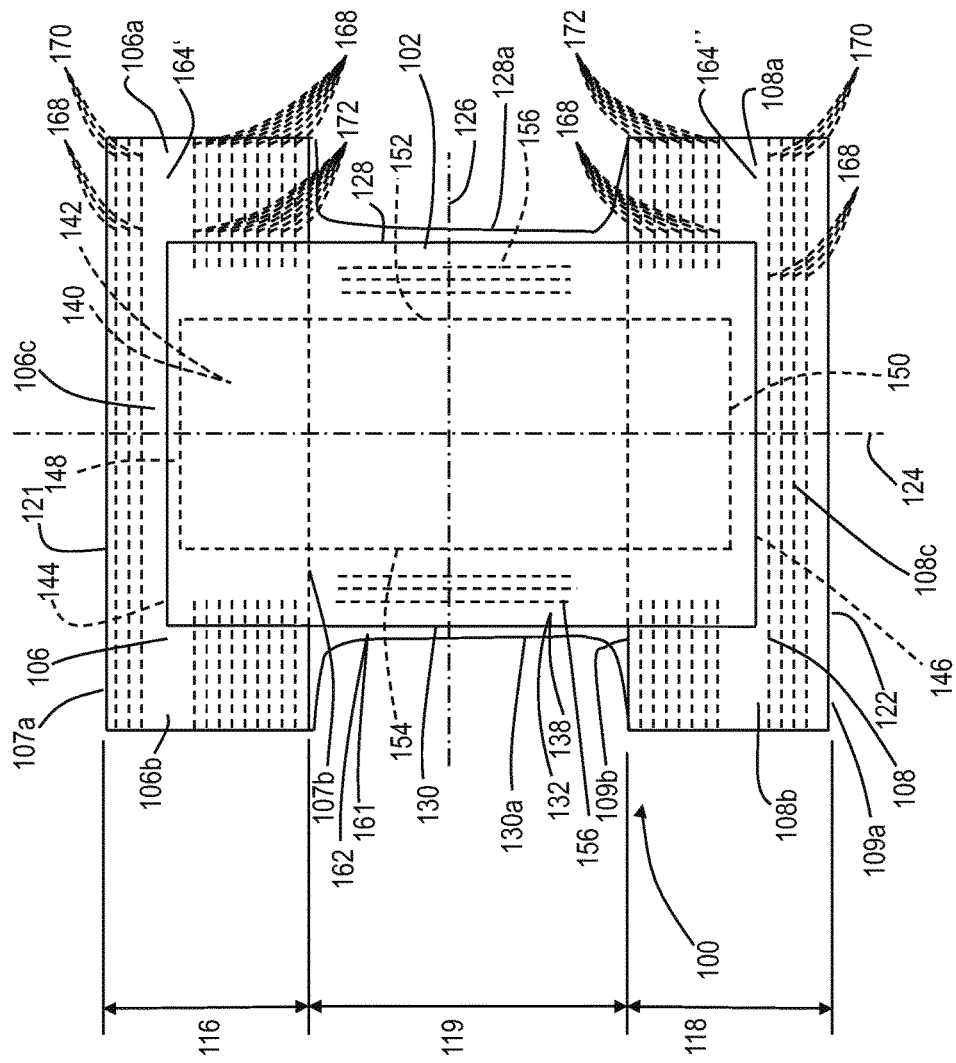

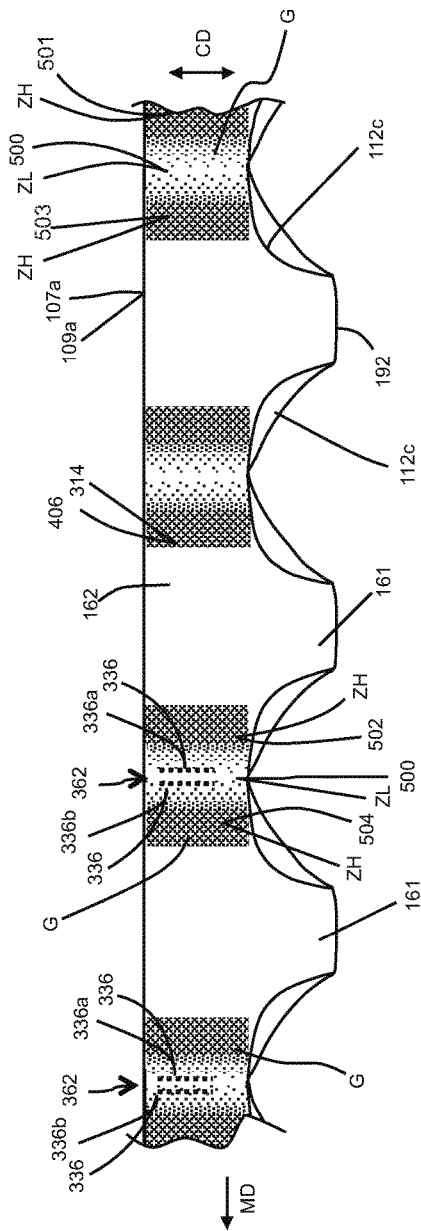
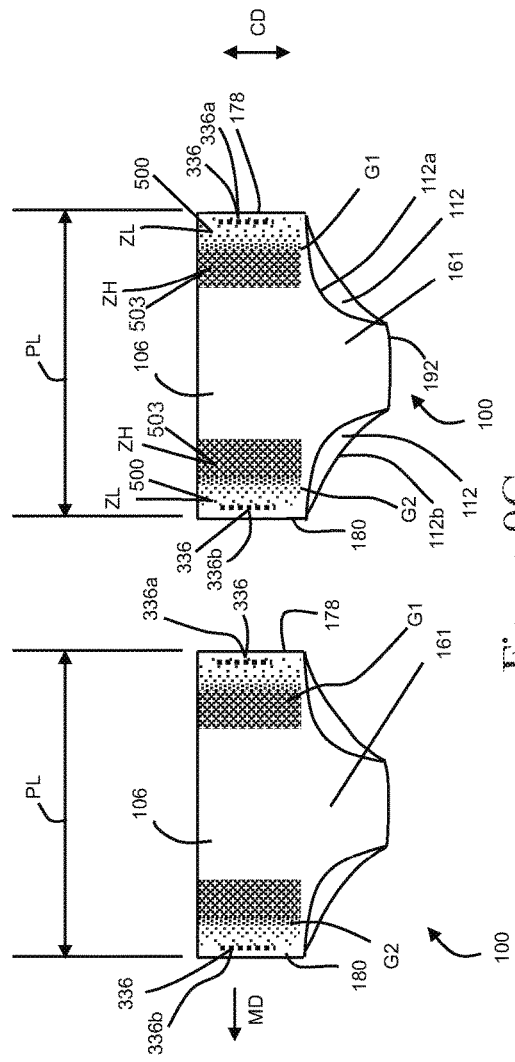
Figure 9F
Figure 9G

APPARATUSES AND METHODS FOR MAKING ABSORBENT ARTICLES WITH LOW INTENSITY SIDE SEAM REGIONS

CROSS REFERENCE TO RELATED APPLICATIONS

This application claims the benefit of U.S. Provisional Application No. 62/093,604 filed on Dec. 18, 2014, which is herein incorporated herein by reference.

FIELD OF THE INVENTION

The present disclosure relates to methods for manufacturing absorbent articles, and more particularly, to assembling absorbent articles with components having graphics including zones of relatively high print densities and zones of relatively low print densities, wherein the zones of relatively low print densities are positioned in regions of assembled components that are subject to various process transformations during assembly.

BACKGROUND OF THE INVENTION

Along an assembly line, diapers and various types of other disposable absorbent articles may be assembled by adding components to and otherwise modifying advancing, continuous webs of material. Webs of material and component parts used to manufacture diapers may include: backsheets, topsheets, absorbent cores, front and/or back ears, fastener components, and various types of elastic webs and components such as leg elastics, barrier leg cuff elastics, and waist elastics.

Some consumers may prefer purchasing absorbent articles, such as diapers, having various types of different graphic designs printed thereon. As such, continuous substrates of material having printed graphics may be converted into different components used to assemble the absorbent articles. During the assembly process, the substrates of material having the graphics printed thereon may be subjected to various process transformations, such as folding, bonding, trimming, and/or cutting.

In some instances, consumers may prefer diapers with graphics defining various designs and various colored areas that may be printed thereon and that may extend over the entire area, or a relatively large area, of the diaper that is visible when worn. Thus, in converting operations involving the assembly of diapers having printed graphics that extend over relatively large regions, the printed substrates may be subjected to various process transformations in areas where the printing is located. However, subjecting printed substrates to various process transformations, such as folding, cutting, bonding, and/or assemblage with other printed components in areas where the graphics are located may create challenges in performing such process transformations when attempting to maintain aesthetically pleasing final assemblies. For example, imprecise and/or inconsistent bonding, cutting, and/or folding operations performed on a substrate in an area where a printed graphic is located may act to visibly highlight such process imprecisions or inconsistencies, such as crooked bond lines, fold lines, and/or cut lines. In another example, imprecise placement of one printed component onto another printed component may be visibly highlighted when graphics on the separate components appear disjointed and/or misaligned when the components are combined. In addition, the aforementioned challenges may be exacerbated in absorbent article assembly processes operating at relatively high speed production rates.

Consequently, there remains a need to incorporate substrates and/or components into absorbent article assembly processes wherein the substrates and/or components include graphics printed and/or positioned in such a manner so as to functionally reduce noticeable visible results of imprecise and/or inconsistent manufacturing operations performed in areas where the graphics are located.

SUMMARY OF THE INVENTION

The present disclosure relates to absorbent articles and methods for assembling absorbent articles with substrates and/or components that include graphics that may be positioned and/or printed in such a manner so as to reduce noticeable visible results of imprecise and/or inconsistent manufacturing operations performed in areas where the graphics are located.

In one form, in a method for assembling disposable diaper pants, each diaper pant comprising a chassis having a first end region and an opposing second end region separated from each other by a central region, and having a longitudinal axis and a lateral axis, the chassis comprising: a topsheet, a backsheet, and an absorbent core disposed between the topsheet and the backsheet, the method comprises the steps of: advancing a first continuous elastic laminate in a machine direction, the first continuous elastic laminate having an outer longitudinal edge and an inner longitudinal edge, the first elastic laminate further comprising a graphic, the graphic extending in the machine direction and comprising a central zone positioned between longitudinally opposing first and second zones, wherein each zone comprises a maximum print density, wherein the maximum print density of the central zone is less than or equal to about 30% of the maximum print densities of the first and second zones, and wherein the central zone defines a length, L, in the machine direction; advancing a second continuous elastic laminate in the machine direction, the second continuous elastic laminate having an outer longitudinal edge and an inner longitudinal edge, wherein the first continuous elastic laminate is separated in the cross direction from the second continuous elastic laminate to define a gap between the inner longitudinal edge of the first continuous elastic laminate and the inner longitudinal edge of the second continuous elastic laminate; depositing a plurality of chassis spaced apart from each other along the machine direction across the gap and onto the first continuous elastic laminate and the second continuous elastic laminate; folding each chassis along the lateral axis to position the first continuous elastic laminate into a facing relationship with the second continuous elastic laminate; and cutting the first and second continuous elastic laminates in the cross direction through the central zone of the graphic and into discrete pieces having a pitch length, PL, extending in the machine direction, wherein the pitch length PL is about 10 or more times the length L of the central zone.

In another form, in a method for assembling disposable diaper pants, each diaper pant comprising a chassis having a first end region and an opposing second end region separated from each other by a central region, and having a longitudinal axis and a lateral axis, the chassis comprising: a topsheet, a backsheet, and an absorbent core disposed between the topsheet and the backsheet, the method comprises the steps of: advancing a continuous elastic laminate in a machine direction, the continuous elastic laminate having a first longitudinal edge and a second longitudinal edge defining a width, W, in a cross direction, the elastic laminate further comprising a graphic, the graphic extending in the machine direction and comprising a central zone positioned between longitudinally opposing first and second zones, wherein each zone comprises a maximum print density, wherein the maximum print density of the central zone is less than or equal to about 30% of the maximum print densities of the first and second zones, and wherein the central zone defines a length, L, in the machine direction; cutting holes in the elastic laminate, wherein the holes spaced apart from each other along the machine direction; depositing a plurality of chassis spaced apart from each other along the machine direction onto the continuous elastic laminate, wherein at least one hole is positioned between two consecutive chassis; folding the continuous elastic laminate and each chassis along the lateral axis to position the first end region of the chassis and the opposing second end region of the chassis into a facing relationship; and cutting the continuous elastic laminate in the cross direction through the central zone of the graphic and into discrete pieces having a pitch length, PL, extending in the machine direction, wherein the pitch length PL is about 10 or more times the length L of the central zone.

In yet another form, an absorbent article comprises: a first elastic belt extending laterally from a first longitudinal side edge to a second longitudinal side edge to define a pitch length, PL, and extending from a first lateral end edge to a second lateral end edge to define a width W, the first elastic belt further comprising a first end region and a laterally opposing second region separated from each other by a central region; a second elastic belt comprising a first end region and a laterally opposing second region separated from each other by a central region, wherein the first end region of the first elastic belt is connected with the first end region of the second elastic belt, and wherein the second end region of the first elastic belt is connected with the second end region of the second elastic belt; a chassis comprising, a topsheet, a backsheet, and an absorbent core disposed between the topsheet and the backsheet, the chassis further comprising a first waist region and a second waist region separated from each other by a crotch region, wherein the first waist region is connected with the central region of the first elastic belt and the second waist region is connected with the central region of the second elastic belt; a graphic on the first elastic belt, the graphic comprising a first zone comprising a first maximum print density and a second zone comprising a second maximum print density, wherein the second maximum print density is less than or equal to about 30% of the first maximum print density; and wherein the second zone is positioned between the first zone and the first longitudinal side edge of the first elastic belt, and wherein the second zone defines a longitudinal length L wherein the pitch length PL is about 10 or more times the length L of the second zone.

BRIEF DESCRIPTION OF THE DRAWINGS

FIG. 2A is a partially cut plan view of the diaper pant shown in FIGS. 1A and 1B in a flat, uncontracted state.
FIG. 3A is a cross-sectional view of the diaper pant of FIG. 2A taken along line 3A-3A.
FIG. 3B is a cross-sectional view of the diaper pant of FIG. 2A taken along line 3B-3B.
FIG. 5A1 is a view of the continuous advancing first substrate from FIG. 5A with an alternative graphic configuration.
FIG. 5A2 is a view of the continuous advancing first substrate from FIG. 5A with an alternative graphic configuration.
FIG. 5C is a view of a continuous length of chassis assemblies from FIGS. 4 and 8 taken along line C-C.
FIG. 5D1 is a view of a discrete chassis from FIGS. 4 and 8 taken along line D1-D1.
FIG. 5D2 is a view of a discrete chassis from FIGS. 4 and 8 taken along line D2-D2.
FIG. 5F is a view of folded multiple discrete chassis with the first and second elastic belt laminates in a facing relationship from FIG. 4 taken along line F-F.
FIG. 5G is a view of two discrete absorbent articles advancing the machine direction MD from FIG. 4 taken along line G-G.
FIG. 6C is a rear plan view of the diaper pant of FIG. 6A.
FIG. 7 is a partially cut plan view of the diaper pant shown in FIGS. 6A-6C in a flat, uncontracted state.
FIG. 9F is a view of folded multiple discrete chassis with the first and second elastic belt laminates in a facing relationship from FIG. 8 taken along line F-F.
FIG. 9G is a view of two discrete absorbent articles advancing the machine direction MD from FIG. 8 taken along line G-G.

DETAILED DESCRIPTION OF THE INVENTION

Figure 1A:
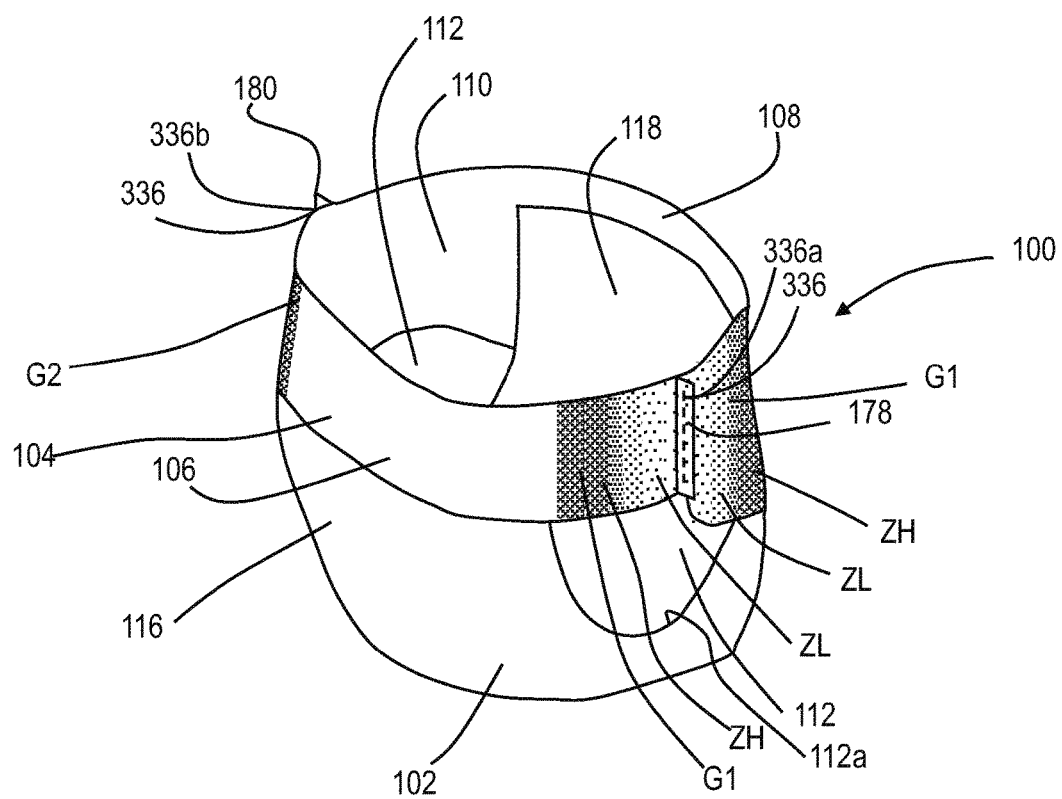
FIG. 1A is a front perspective view of a diaper pant.

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

An "elastic," "elastomer" or "elastomeric" refers to materials exhibiting elastic properties, which include any material that upon application of a force to its relaxed, initial length can stretch or elongate to an elongated length more than 10% greater than its initial length and will substantially recover back to about its initial length upon release of the applied force.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

As used herein, the term "graphic" refers to printed areas of substrates. Graphics may include a color difference or transition of one or more colors and may define images or designs that are constituted by a figure (for example, a line(s)), a symbol or character), or the like. A graphic may include an aesthetic image or design that can provide certain benefit(s) when viewed. A graphic may be in the form of a photographic image. A graphic may also be in the form of a 1-dimensional (1-D) or 2-dimensional (2-D) bar code or a quick response (QR) bar code. A graphic design is determined by, for example, the color(s) used in the graphic (individual pure ink or spot colors as well as built process colors), the sizes of the entire graphic (or components of the graphic), the positions of the graphic (or components of the graphic), the movements of the graphic (or components of the graphic), the geometrical shapes of the graphic (or components of the graphics), the number of colors in the graphic, the variations of the color combinations in the graphic, the number of graphics printed, the disappearance of color(s) in the graphic, and the contents of text messages in the graphic.

It is to be appreciated that all graphics discussed herein may be in various different forms, shapes, and/or sizes than those depicted herein. It is also to be appreciated that the graphics described herein may be configured to be different graphics, standard graphics, custom graphics, and/or personalized graphics. "Different in terms of graphic design" means that graphics are intended to be different when viewed by users or consumers with normal attentions. Thus, two graphics having a graphic difference(s) which are unintentionally caused due to a problem(s) or an error(s) in a manufacture process, for example, are not different from each other in terms of graphic design. "Standard" or "standardized" refers to graphics, products, and/or articles that have the same aesthetic appearance without intending to be different from each other. The term "custom" or "customized" refers to graphics, products, and/or articles that are changed to suit a small demographic, region, purchaser, customer, or the like. Custom graphics may be selected from a set of graphics. For example, custom graphics may include animal depictions selected from groups of animals, such as farm animals, sea creatures, birds, and the like. In other examples, custom graphics may include nursery rhymes and the like. In one scenario, custom products or articles may be created by a purchaser of such products or articles wherein the purchaser selects graphics for the articles or products from a set of graphics offered by a manufacturer of such articles or products. Custom graphics may also include "personalized" graphics, which may be graphics created for a particular purchaser. For example, personalized graphics may include a person's name alone or in combination with a design.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

The term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed).

The term "print density," which may also be referred to optical density, refers to the reflection density of printed matter, as measured with a spectrophotometer in accordance with the Method for Measuring Print Color and Print Density provided herein.

The present disclosure relates to absorbent articles and methods for assembling absorbent articles with components having printed graphics including zones of relatively high print densities and zones of relatively low print densities. More particularly, substrates and/or components to be incorporated into manufactured absorbent articles herein include graphics that may be positioned and/or printed in such a manner so as to functionally reduce noticeable visible results of imprecise and/or inconsistent manufacturing operations performed in areas where the graphics are located. For example, the substrates and/or components include graphics wherein the zones of relatively low print densities may be positioned in regions that are subject to bonding, cutting, and/or folding transformations during the assembly process. In addition, the zones of relatively high print densities may be positioned regions that may be more noticeable to consumers. For example, assembled diapers may include graphics with zones of relatively low print density zones positioned in side seam regions, whereas the relatively high print density zones may be positioned closer to central portions of front and/or back waist regions. Thus, the methods and apparatuses herein allow for the assemblage of substrates and/or components having graphics defining various designs and various colored areas printed thereon that extend over the entire area, or a relatively large area, of the assembled diapers that is visible when worn while maintaining desired aesthetic benefits on assembled diapers without sacrificing relatively high manufacturing speeds.

As previously mentioned, the processes and apparatuses discussed herein may be used in the manufacture of different types of absorbent articles. To help provide additional context to the subsequent discussion of the process embodiments, the following provides a general description of absorbent articles in the form of diaper pants that include belt substrates that may be assembled in accordance with the methods and apparatuses disclosed herein.

Figure 1B:
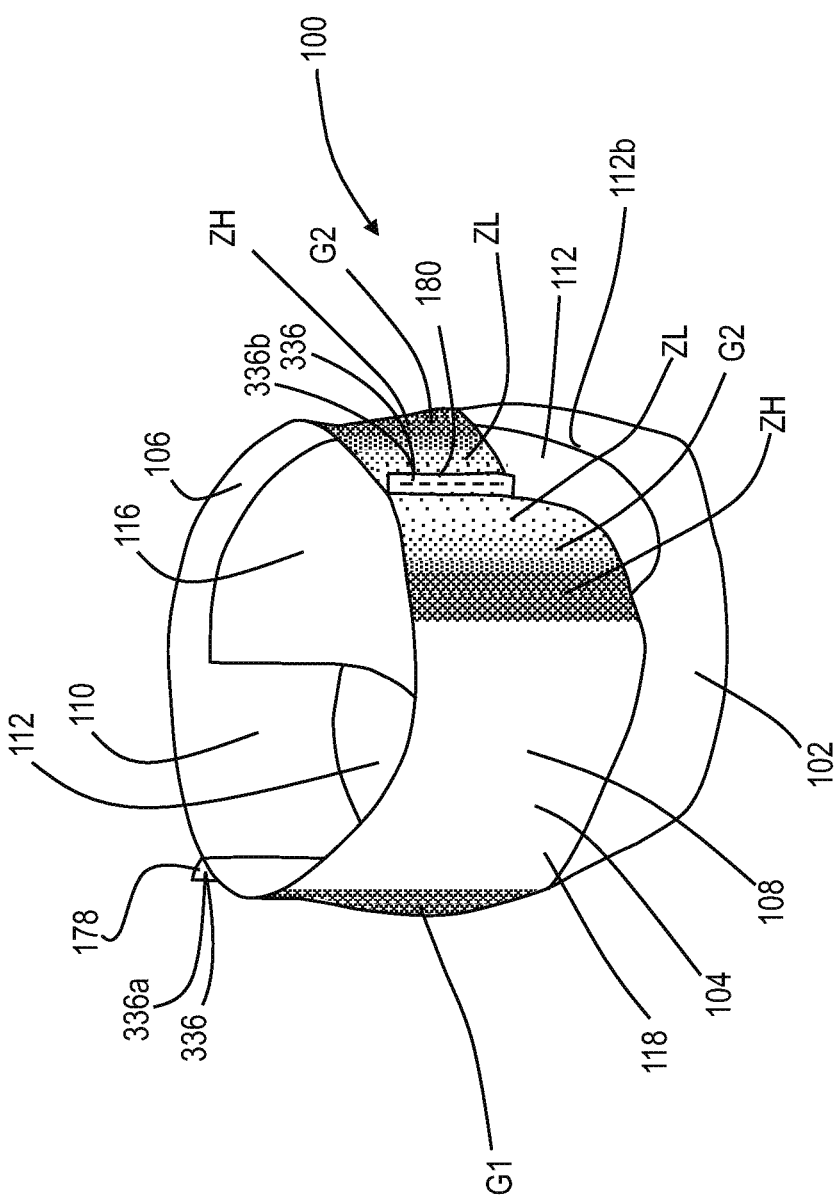
FIG. 1B is a rear perspective view of a diaper pant.
Figure 2B:
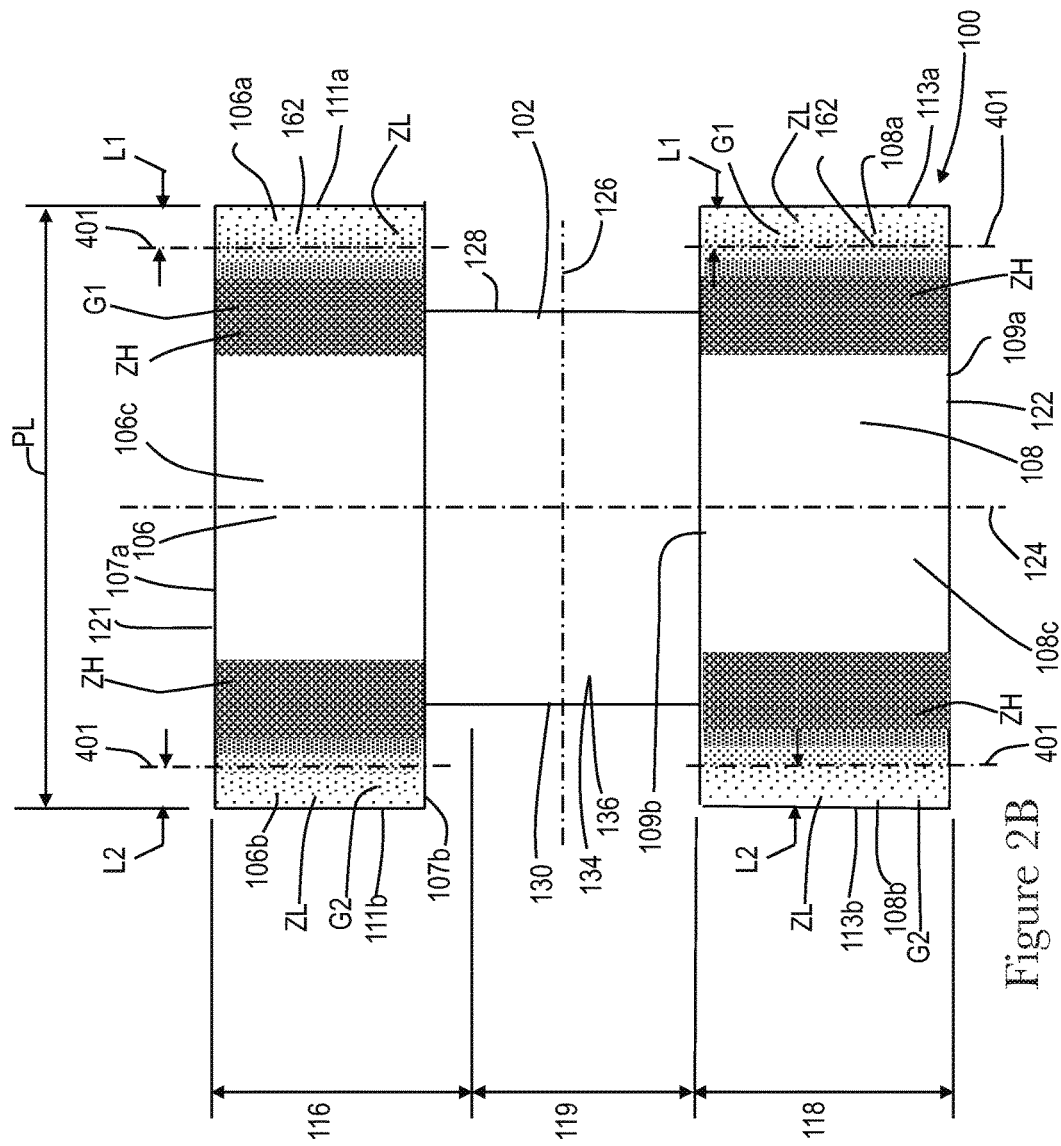
FIG. 2B is a plan view of the diaper pant shown in FIGS. 1A and 1B in a flat, uncontracted state and including graphics with low intensity zones positioned along opposing end edges of front and back belts.

FIGS. 1A, 1B, 2A, and 2B show an example of a diaper pant 100 that may be assembled in accordance with the apparatuses and methods disclosed herein. In particular, FIGS. 1A and 1B show perspective views of a diaper pant 100 in a pre-fastened configuration, and FIGS. 2A and 2B show plan views of the diaper pant 100 with the portion of the diaper that faces from a wearer oriented toward the viewer. The diaper pant 100 includes a chassis 102 and a ring-like elastic belt 104. As discussed below in more detail, a first elastic belt 106 and a second elastic belt 108 are bonded together to form the ring-like elastic belt 104.

With continued reference to FIGS. 2A and 2B, the diaper pant 100 and the chassis 102 each include a first waist region 116, a second waist region 118, and a crotch region 119 disposed intermediate the first and second waist regions. The first waist region 116 may be configured as a front waist region, and the second waist region 118 may be configured as back waist region. In some embodiments, the length of each of the front waist region, back waist region, and crotch region may be ⅓ of the length of the absorbent article 100. The diaper 100 may also include a laterally extending front waist edge 121 in the front waist region 116 and a longitudinally opposing and laterally extending back waist edge 122 in the back waist region 118. To provide a frame of reference for the present discussion, the diaper 100 and chassis 102 of FIGS. 2A and 2B are shown with a longitudinal axis 124 and a lateral axis 126. In some embodiments, the longitudinal axis 124 may extend through the front waist edge 121 and through the back waist edge 122. And the lateral axis 126 may extend through a first longitudinal or right side edge 128 and through a midpoint of a second longitudinal or left side edge 130 of the chassis 102.

As shown in FIGS. 1A, 1B, 2A, and 2B, the diaper pant 100 may include an inner, body facing surface 132, and an outer, garment facing surface 134. The chassis 102 may include a backsheet 136 and a topsheet 138. The chassis 102 may also include an absorbent assembly 140, including an absorbent core 142, disposed between a portion of the topsheet 138 and the backsheet 136. As discussed in more detail below, the diaper 100 may also include other features, such as leg elastics and/or leg cuffs to enhance the fit around the legs of the wearer.

As shown in FIGS. 2A and 2B, the periphery of the chassis 102 may be defined by the first longitudinal side edge 128, a second longitudinal side edge 130, a first laterally extending end edge 144 disposed in the first waist region 116, and a second laterally extending end edge 146 disposed in the second waist region 118. Both side edges 128 and 130 extend longitudinally between the first end edge 144 and the second end edge 146. As shown in FIG. 2A, the laterally extending end edges 144 and 146 are located longitudinally inward from the laterally extending front waist edge 121 in the front waist region 116 and the laterally extending back waist edge 122 in the back waist region 118. When the diaper pant 100 is worn on the lower torso of a wearer, the front waist edge 121 and the back waist edge 122 may encircle a portion of the waist of the wearer. At the same time, the side edges 128 and 130 may encircle at least a portion of the legs of the wearer. And the crotch region 119 may be generally positioned between the legs of the wearer with the absorbent core 142 extending from the front waist region 116 through the crotch region 119 to the back waist region 118.

It is to also be appreciated that a portion or the whole of the diaper 100 may also be made laterally extensible. The additional extensibility may help allow the diaper 100 to conform to the body of a wearer during movement by the wearer. The additional extensibility may also help, for example, the user of the diaper 100, including a chassis 102 having a particular size before extension, to extend the front waist region 116, the back waist region 118, or both waist regions of the diaper 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the diaper pant 100 may include a backsheet 136. The backsheet 136 may also define the outer surface 134 of the chassis 102. The backsheet 136 may be impervious to fluids (e.g., menses, urine, and/or runny feces) and may be manufactured in part from a thin plastic film, although other flexible liquid impervious materials may also be used. The backsheet 136 may prevent the exudates absorbed and contained in the absorbent core from wetting articles which contact the diaper 100, such as bedsheets, pajamas and undergarments. The backsheet 136 may also comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also comprise an elastomeric film. An example backsheet 136 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the diaper 100.

Also described above, the diaper pant 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539.

As mentioned above, the diaper pant 100 may also include an absorbent assembly 140 that is joined to the chassis 102. As shown in FIG. 2A, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprises primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 and 2004/0097895.

As previously mentioned, the diaper 100 may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; 4,704,115; 4,909,803; and U.S. Patent Publication No. 2009/0312730 A1.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, diaper pants may have a continuous perimeter waist opening 110 and continuous perimeter leg openings 112 such as shown in FIGS. 1A and 1B. The ring-like elastic belt may be formed by joining a first elastic belt to a second elastic belt with a permanent side seam or with an openable and reclosable fastening system disposed at or adjacent the laterally opposing sides of the belts.

As previously mentioned, the ring-like elastic belt 104 may be defined by a first elastic belt 106 connected with a second elastic belt 108. As shown in FIGS. 2A and 2B, the first elastic belt 106 extends between a first longitudinal side edge 111a and a second longitudinal side edge 111b and defines first and second opposing end regions 106a, 106b and a central region 106c. And the second elastic 108 belt extends between a first longitudinal side edge 113a and a second longitudinal side edge 113b and defines first and second opposing end regions 108a, 108b and a central region 108c. The distance between the first longitudinal side edge 111a and the second longitudinal side edge 111b defines the pitch length, PL, of the first elastic belt 106, and the distance between the first longitudinal side edge 113a and the second longitudinal side edge 113b defines the pitch length, PL, of the second elastic belt 108. The central region 106c of the first elastic belt is connected with the first waist region 116 of the chassis 102, and the central region 108c of the second elastic belt 108 is connected with the second waist region 116 of the chassis 102. As shown in FIGS. 1A and 1B, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

It is to be appreciated that the first and second elastic belts may define various pitch lengths PL. For example, in some embodiments, the pitch lengths PL of the first and/or second elastic belts 106, 108 may be about 300 mm to about 1000 mm.

As shown in FIGS. 2A, 3A, and 3B, the first elastic belt 106 also defines an outer laterally extending edge 107a and an inner laterally extending edge 107b, and the second elastic belt 108 defines an outer laterally extending edge 109a and an inner laterally extending edge 109b. As such, a perimeter edge 112a of one leg opening may be defined by portions of the inner laterally extending edge 107b of the first elastic belt 106, the inner laterally extending edge 109b of the second elastic belt 108, and the first longitudinal or right side edge 128 of the chassis 102. And a perimeter edge 112b of the other leg opening may be defined by portions of the inner laterally extending edge 107b of the first elastic belt 106, the inner laterally extending edge 109b of the second elastic belt 108, and the second longitudinal or left side edge 130 of the chassis 102. The outer laterally extending edges 107a, 109a may also define the front waist edge 121 and the laterally extending back waist edge 122 of the diaper pant 100. The first elastic belt and the second elastic belt may also each include an outer, garment facing layer 162 and an inner, wearer facing layer 164. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts include a nonwoven web of synthetic fibers, and may include a stretchable nonwoven. In other embodiments, the first and second elastic belts include an inner hydrophobic, non-stretchable nonwoven material and an outer hydrophobic, non-stretchable nonwoven material.

The first and second elastic belts 106, 108 may also each include belt elastic material interposed between the outer substrate layer 162 and the inner substrate layer 164. The belt elastic material may include one or more elastic elements such as strands, ribbons, films, or panels extending along the lengths of the elastic belts. As shown in FIGS. 2A, 3A, and 3B, the belt elastic material may include a plurality of elastic strands 168 which may be referred to herein as outer, waist elastics 170 and inner, waist elastics 172. Elastic strands 168, such as the outer waist elastics 170, may continuously extend laterally between the first and second opposing end regions 106a, 106b of the first elastic belt 106 and between the first and second opposing end regions 108a, 108b of the second elastic belt 108. In some embodiments, some elastic strands 168, such as the inner waist elastics 172, may be configured with discontinuities in areas, such as for example, where the first and second elastic belts 106, 108 overlap the absorbent assembly 140. In some embodiments, the elastic strands 168 may be disposed at a constant interval in the longitudinal direction. In other embodiments, the elastic strands 168 may be disposed at different intervals in the longitudinal direction. The belt elastic material in a stretched condition may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt. It is to be appreciated that the chassis 102 and elastic belts 106, 108 may be configured in different ways other than as depicted in FIG. 2A. The belt elastic material may be joined to the outer and/or inner layers continuously or intermittently along the interface between the belt elastic material and the inner and/or outer belt layers.

In some configurations, the first elastic belt 106 and/or second elastic belt 108 may define curved contours. For example, the inner lateral edges 107b, 109b of the first and/or second elastic belts 106, 108 may include non-linear or curved portions in the first and second opposing end regions. Such curved contours may help define desired shapes to leg opening 112, such as for example, relatively rounded leg openings. In addition to having curved contours, the elastic belts 106, 108 may include elastic strands 168, 172 that extend along non-linear or curved paths that may correspond with the curved contours of the inner lateral edges 107b, 109b.

As previously mentioned, the diaper pant 100 may include one or more graphics. And such graphics may include zones of relatively high print densities, referred to herein as "high intensity zones," and zones of relatively low print densities, referred to herein as "low intensity zones." As discussed above, the diaper components may include graphics positioned and/or printed in such a manner so as to reduce noticeable visible results of imprecise and/or inconsistent manufacturing operations performed in areas where the printing is located. Thus, the high intensity zones may be positioned in regions of the diaper that may be more noticeable to consumers. And the low intensity zones may be positioned in regions that are subject to cutting and/or folding transformations during the assembly process, such as side seam regions. With respect to the graphics discussed herein, each zone comprises a maximum print density, and the maximum print density of the low intensity zone is greater than zero and less than the maximum print density of the high intensity zone. For example, in some embodiments, the maximum print density of the high intensity zone may be at least about 0.3; 0.4; or 0.5. And in some embodiments, the maximum print density of the low intensity zone may be greater than zero and less than or equal to about 0.15 or 0.1. In some embodiments, the maximum print density of the low intensity zone may be less than or equal to about 30% of the maximum print density of the high intensity zone. In some embodiments, the maximum print density of the low intensity zone may be less than or equal to about 25% of the maximum print density of the high intensity zone. In some embodiments, the maximum print density of the low intensity zone may be less than or equal to about 10% of the maximum print density of the high intensity zone. In addition, the graphics may be printed so as to fade from the high intensity zone to the low intensity zone. As used herein, the term "fade" means a visible gradual change in color hue, brightness, lightness, chroma, and/or saturation, for example, when a graphic fades from an area having a relatively high print density to an area having a relatively low print density.

It is to be appreciated that the graphics described herein may be printed in various ways and may be printed by various types of printing accessories, such as ink jet, flexography, and/or gravure printing processes. Ink-jet printing is a non-impact dot-matrix printing technology in which droplets of ink are jetted from a small aperture directly to a specified position on a media to create a graphic. Two examples of inkjet technologies include thermal bubble or bubble jet and piezoelectric. Thermal bubble uses heat to apply to the ink, while piezoelectric uses a crystal and an electric charge to apply the ink. In some configurations, the printing stations may include a corona treater, which may be positioned upstream of the printer. The corona treater may be configured to increase the surface energy of the surface of the substrate to be printed. In some configurations, the printing stations may also include an ink curing apparatus. In some configurations, the ink curing apparatus may be in the form of an ultraviolet (UV) light source that may include one or more ultraviolet (UV) lamps, which may be positioned downstream of the printer to help cure inks deposited onto the substrate from the printer to form the graphics. In some configurations, the ink curing apparatus may also include an infrared (IR) dryer light source that may include one or more infrared (IR) lamps, which may be positioned downstream of the printer to help dry water-based or solvent-based inks deposited onto the substrate to form the graphics. In some configurations, the ink curing apparatus may include an electron beam (EB or e-beam) generator that may include one or more e-beam electrodes, which may be positioned downstream of the printer to help cure inks deposited onto the substrate from the printer to form the graphics.

FIGS. 1A, 1B, and 2B show an example diaper pant 100 with printed graphics G1, G2 on the first elastic belt 106 and the second elastic belt 108, wherein each graphic includes a high intensity zone ZH and a low intensity zone ZL. As shown in FIG. 2B, the low intensity zones ZL are positioned in the opposing end regions 106a, 106b of the first belt 106 as well as the opposing end regions of 108a, 108b of the second belt 108. As discussed in more detail below, the end regions of the belts 106, 108 where the low intensity zones ZL are located, may be subject to cutting and seaming process operations during the assembly process. In addition, the high intensity zones ZH are positioned relatively closer to the central regions 106c, 108c of the first and second belts 106, 108.

With continued reference to FIGS. 1A, 1B, and 2B, the low intensity zone ZL of the graphic G1 on the front belt 106 is positioned between the high intensity zone ZH and the first longitudinal side edge 111a, and the low intensity zone ZL of the graphic G2 on the front belt 106 is positioned between the high intensity zone ZH and the second longitudinal side edge 111b. For the purposes of clarity, dashed lines 401 are shown in FIG. 2B to represent example boundaries between the high intensity zones ZH and the low intensity zones ZL. It is to be appreciated that such boundaries between the high intensity zones ZH and the low intensity zones ZL can also be curved, angled, and/or straight. As shown in FIG. 2B, the low intensity zone ZL of the graphic G1 on the front belt 106 may extend from the high intensity zone ZH entirely to the first longitudinal side edge 111a, and the low intensity zone ZL of the graphic G2 on the front belt 106 may extend from the high intensity zone ZH entirely to the second longitudinal side edge 111b. It is to be appreciated that in some embodiments, the low intensity zones ZL may not extend all the way to the first and second edges 111a, 111b. As also shown in FIG. 2B, the low intensity zones ZL of the graphic G1 and graphic G2 on the front belt 106 may extend entirely from the outer laterally extending edge 107a to the inner laterally extending edge 107b of the first belt 106. It is to be appreciated that in some embodiments, the low intensity zones ZL may not extend all the way to one of or both of the inner and outer lateral edges 107a, 107b.

As previously discussed, the low intensity zones ZL are positioned in regions of the diapers 100 that may be subject to various cutting and/or folding transformations during the assembly process so as to reduce noticeable visible results of imprecisions and/or inconsistencies of such transformations. Thus, it is also to be appreciated that the low intensity zones ZL discussed herein may be devoid of additional graphics. As such, it may be desirable in some embodiments to manufacture absorbent articles with graphics having a high intensity zone and a low intensity zone wherein the low intensity zone is devoid of any other printed graphics or the like.

As shown in FIG. 2B, the low intensity zone ZL of the first graphic G1 may define a length L1 along the first belt 106 and the second belt 108, and the low intensity zone ZL of the second graphic G2 may define a length L2 along the first belt 106 and the second belt 108. It is to be appreciated that lengths L1, L2 of the low intensity zones ZL may vary. In some embodiments, the lengths L1 and/or L2 may be from about 5 mm to about 30 mm. In some embodiments, the lengths L1, L2 may be expressed in terms relative to the pitch lengths PL of the first and/or second belts 106, 108. For example, in some embodiments, the pitch lengths PL of the first and/or second belts 106, 108 may be about 20 to about 100 times the lengths L1 and/or L2.

Figure 4:
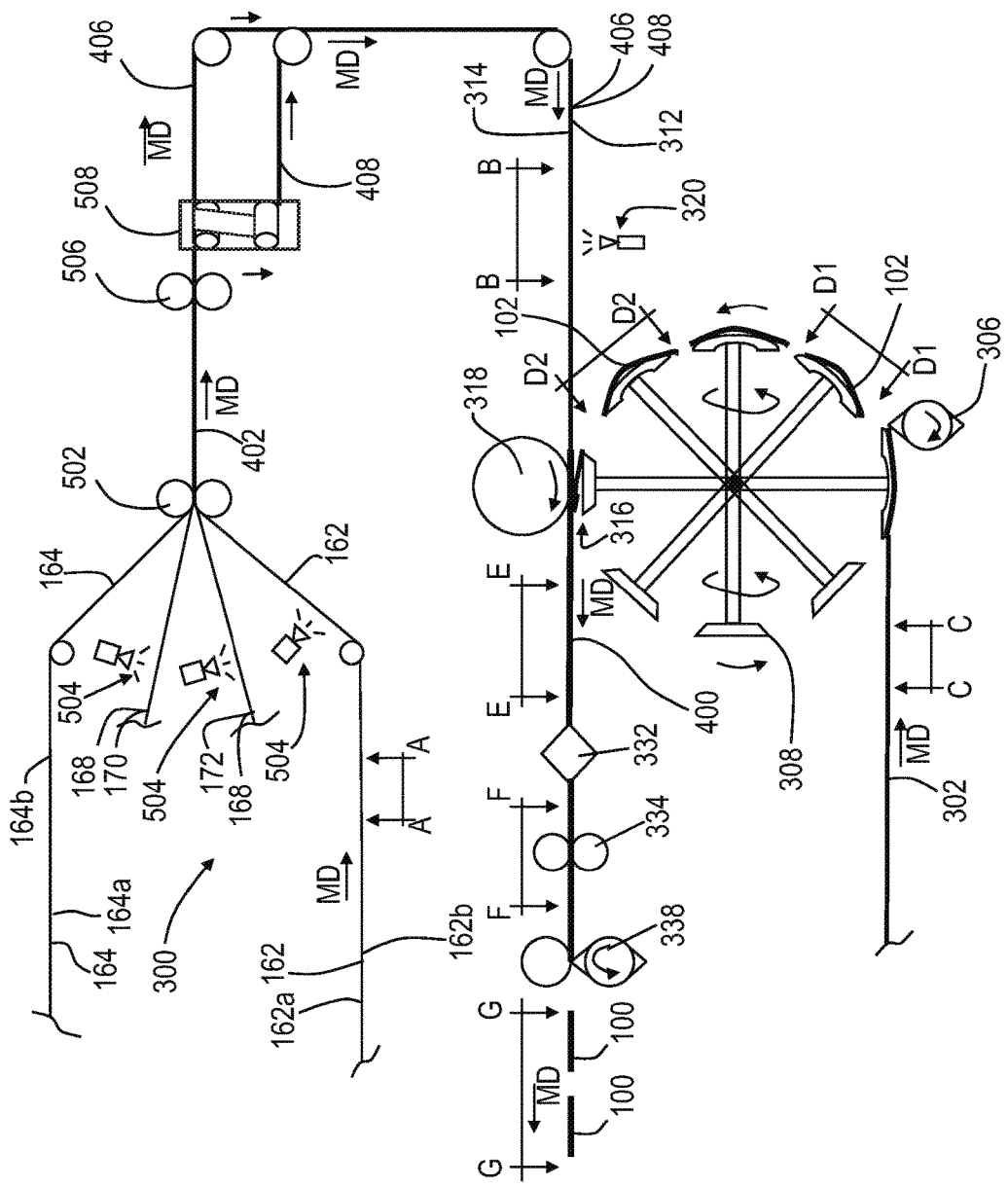
FIG. 4 is a schematic side view of a converting apparatus adapted to manufacture pre-fastened, pant diapers.

As previously mentioned, substrates and/or components that may be incorporated into manufactured absorbent articles, such as shown in FIG. 2B, include graphics that may be positioned and/or printed in such a manner so as to reduce noticeable visible results of imprecise and/or inconsistent manufacturing operations performed in areas where the printing is located. It is to be appreciated that various apparatuses and methods according to the present disclosure may be utilized to assemble various components of pre-fastened pant diapers 100 described herein. For example, FIG. 4 shows a schematic view of a converting apparatus 300 adapted to manufacture pant diapers 100. The method of operation of the converting apparatus 300 may be described with reference to the various components of pant diapers 100 described above and shown in FIGS. 1A, 1B, 2A, and 2B. Although the following methods are provided in the context of the diaper 100 shown in FIGS. 1A, 1B, 2A, and 2B, it is to be appreciated that various embodiments of diaper pants can be manufactured according to the methods disclosed herein, such as for example, the absorbent articles disclosed in U.S. Pat. No. 7,569,039; U.S. Patent Publication Nos. 2005/0107764 A1, 2012/0061016 A1, and 2012/0061015 A1, which are all hereby incorporated by reference herein.

As described in more detail below, the converting apparatus 300 shown in FIG. 4 operates to advance first and second elastic belt laminates 406, 408 along a machine direction MD. In addition, a continuous length of chassis assemblies 302 are advanced in a machine direction MD and cut into discrete chassis 102 such that the longitudinal axis 124 of each chassis 102 is parallel with the machine direction MD. The discrete chassis 102 are then turned to advance the discrete chassis 102 along the machine direction MD such that the lateral axis 126 of each chassis 102 is parallel with the machine direction MD. The discrete chassis 102 are also spaced apart from each other along the machine direction MD. Opposing waist regions 116, 118 of the spaced apart chassis 102 are then connected with continuous lengths of advancing first and second elastic belt laminates 406, 408. The chassis 102 may then be folded along the lateral axis, or parallel to the lateral axis, to bring the first and second elastic belt laminates 406, 408 into a facing relationship, and the first and second elastic belt laminates are bonded together with laterally opposing bonds 336. As discussed in more detail below, the first and second elastic belt laminates may be bonded together with adjacent bonds 336a, 336b intermittently spaced along the machine direction MD. It is to be appreciated that the bonds 336a, 336b may be configured as permanent and/or refastenable bonds. And each bond 336a, 336b may be a discrete bond site extending contiguously in a cross direction CD across a width of the first and second elastic belt laminates and/or may include a plurality of relatively small, discrete bond sites arranged in the cross direction. The first and second continuous elastic laminates 406, 408 are then cut in the cross direction CD between adjacent bonds 336a, 336b to create discrete pant diapers 100, such as shown in FIGS. 1A and 1B.

As shown in FIG. 4, a first continuous substrate layer in the form of a continuous length of outer layer belt substrate 162; a second continuous substrate layer in the form of a continuous length of inner layer belt substrate 164; and elastics 168 are combined to form a continuous elastic laminate 402 in the form of a belt material. More particularly, continuous lengths of outer layer belt substrate 162, inner layer belt substrate 164, outer elastic strands 170 and inner elastic strands 172 are advanced in a machine direction MD and combined at nip rolls 502 to form the continuous elastic laminate 402. Before entering the nip rolls 502, the outer layer belt substrate 162 and/or the inner layer belt substrate 164 may be printed with graphics having high intensity zones and low intensity zones as discussed above. It is to be appreciated that the graphic printing may be done during the assembly process and/or may done separate to the assembly process, such as for example, printing the substrates off line wherein the printed substrates may be stored until needed for production.

Figure 5A:
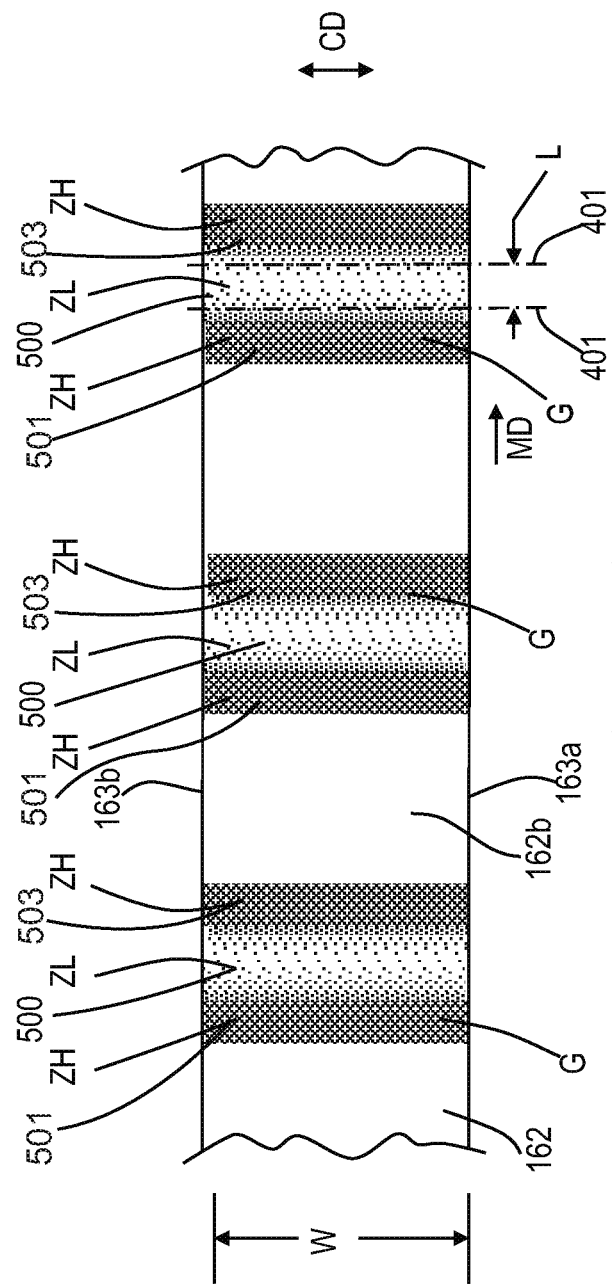
FIG. 5A is a view of a continuous length of an advancing first substrate from FIG. 4 taken along line A-A.

As shown in FIGS. 4 and 5A, the outer belt substrate 162 includes first surface 162a and an opposing second surface 162b, and defines a width W in the cross direction between opposing longitudinal edges 163a, 163b. And the outer belt substrate 162 may advance in the machine direction MD and may include graphics G printed on the first surface 162a of the outer layer belt substrate 162. As shown in FIG. 5A, although the graphics G are printed on the first surface 162a of the outer layer belt substrate 162, the graphics G may be visible through the second surface 162b. It is also to be appreciated that the graphics G may be printed on either or both the first and second surfaces 162a, 162b of the outer belt substrate 162. It is also to be appreciated that graphics may be printed on either or both the first and second surfaces 164a, 164b of the inner belt substrate 164.

As shown in FIG. 5A, each graphic G extends in the machine direction and includes a central zone 500 positioned between longitudinally opposing first and second zones 501, 503. The central zone 500 is a low intensity zone ZL and the first and second zones 501, 503 are high intensity zones ZH. For the purposes of clarity, dashed lines 401 are shown in FIG. 5A to represent example boundaries between the high intensity zones ZH and the low intensity zones ZL. It is to be appreciated that such boundaries between the high intensity zones ZH and the low intensity zones ZL can also be curved, angled, and/or straight. As shown in FIG. 5A, the central zone 500 defines a length, L, in the machine direction MD. It is to be appreciated that lengths L of the central zones 500 may vary. In some embodiments, the lengths L may be from about 10 mm to about 60 mm. In some embodiments, the lengths L may also be expressed in terms relative to the pitch lengths PL of the first and second belts 106, 108 of the assembled diapers 100. For example, in some embodiments, the pitch lengths PL of the first and/or second belts 106, 108 may be about 10 mm to about 25 times the length L. In addition, the central zone 500 and the first and second zones extend in the cross direction CD for the entire width W of the outer belt substrate 162. It is to be appreciated that in some embodiments, the central zone 500 and/or the first and second zones may extend in the cross direction CD for less than the entire width W.

Although FIG. 5A depicts consecutive first and second zones 501, 503 as being separate from each other, it is to be appreciated that the graphics G may be printed such that the consecutive first and second zones may be contiguous, such as shown for example in FIG. 5A1. As such, FIG. 5A1 shows an embodiment with contiguous high intensity zones ZH extending along the machine direction MD, wherein the high intensity zones ZH are separated from each other by low intensity zones ZL extending along the machine direction MD. It is to also to be appreciated that the graphics G may be printed to have differing designs from each other along the machine direction and/or cross direction, such as shown for example in FIG. 5A2.

Referring back to FIG. 4, before entering the nip rolls 502, the outer elastic strands 170 and inner elastic strands 172 are stretched in the machine direction MD. In addition, adhesive 504 may be applied to the elastic strands 170, 172 as well as either or both of the continuous lengths of outer layer belt substrate 162 and inner layer belt substrate 164 before entering nip rolls 502. As such, the elastic strands 168 are bonded between the first surface 162a of the outer layer belt substrate 162 and the first surface 164a of inner layer belt substrate 164 at the nip rolls 502. Further, adhesive 504 may be applied intermittently along the lengths of the inner elastic strands 172 and/or intermittently along the length of either or both of the continuous lengths of outer layer belt substrate 162 and inner layer belt substrate 164 before entering nip rolls 502. As such, the inner elastic strands 172 may be intermittently bonded to either or both of the continuous lengths of outer layer belt substrate 162 and inner layer belt substrate 164 along the machine direction MD. Thus, the continuous elastic laminate 402 may include non-bonded regions intermittently spaced between bonded regions along the machine direction MD, wherein the inner elastic strands 172 are not bonded to either the outer layer belt substrate 162 or inner layer belt substrate 164 in the non-bonded regions. And the inner elastic strands 172 are bonded to the outer layer belt substrate 162 and/or inner layer belt substrate 164 in the bonded regions. As such, the elastic strands 172 may be severed in the non-bonded regions in a subsequent process step. Although FIG. 4 shows an embodiment wherein the continuous elastic laminate 402 is formed by combining continuous lengths of outer layer belt substrate 162 and inner layer belt substrate 164 with elastic strands 168, it is to be appreciated the continuous elastic laminate 402 can be formed in various ways, such as disclosed in U.S. Pat. No. 8,440,043 and U.S. Patent Publication Nos. 2013/0255861 A1; 2013/0255862 A1; 2013/0255863 A1; 2013/0255864 A1; and 2013/0255865 A1.

Figure 5B:
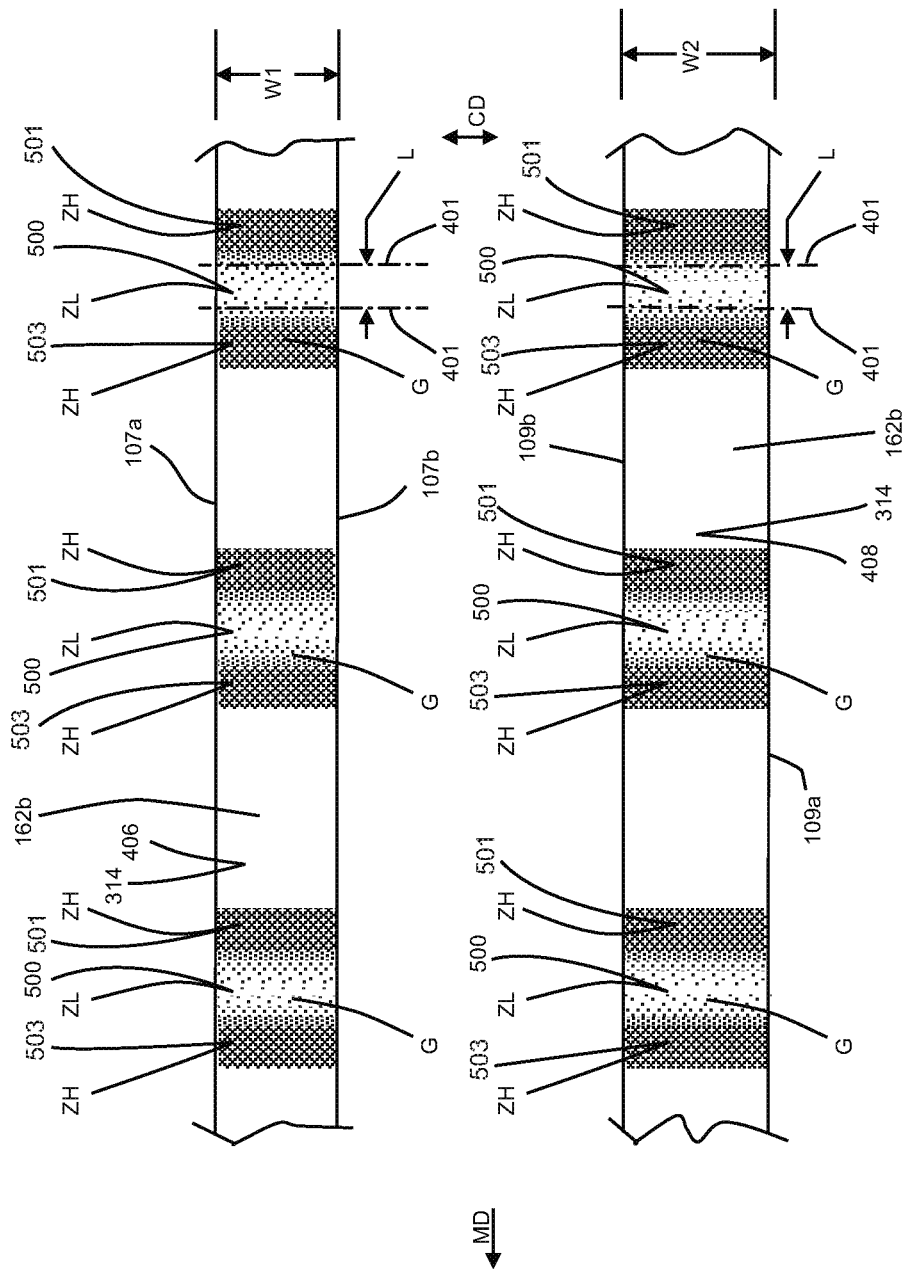
FIG. 5B is a view of continuous lengths of advancing first and second elastic belt laminates from FIG. 4 taken along line B-B.

With continued reference to FIG. 4, from the nip rolls 502 the continuous elastic laminate 402 advances in the machine direction MD to a cutter 506 that cuts the continuous elastic laminate 402 into two continuous elastic belt laminates, referred to as a first elastic belt laminate 406 and a second elastic belt laminate 408. The cutter 506 may be configured in various ways. For example, in some embodiments the cutter 506 may be a slitter or a die cutter that separates the belt material into two continuous belt substrates with either a straight line cut and/or a curved line cut. The cutter 506 may also be configured as a perforator that perforates the belt material with a line of weakness and wherein the belt material is separated along the line of weakness in a later step. From the cutter 506, the first and second belt laminates 406, 408 advance through a diverter 508 that separates the first and second belt substrates from each other in the cross direction CD, such as shown in FIG. 5B. The elastic strands 170, 172, and thus, the continuous length of first and second belt laminates 406, 408 are maintained in a stretched condition while advancing along the machine direction MD. It is to be appreciated that the diverter 508 may be configured in various ways. For example, in some embodiments, the diverter 508 may include turn bars angled at 45 degrees or some other angle with respect to the machine direction. In some embodiments, the diverter may include cambered rollers. It is to be appreciated that the front and back belts may be formed by separate continuous lengths of belt material similar to the description above and as such would not required the slitting step or the diverting step.

In some embodiments, the diverter 508 may include a pivot or tracking table, such as for example, the FIFE-500 Web Guiding System, by Maxcess-FIFE Corporation, which can adjust the positions of the continuous length of first and second belt laminates 406, 408 in the cross direction CD. Other suitable pivot or tracking tables are available from Erhardt & Leimer, Inc. The diverter may also include instrumentation and web edge control features that allow for precise active control of the substrate positions.

As shown in FIG. 5B, the first belt laminate 406 includes an outer longitudinal edge 107a and an inner longitudinal edge 107b that may define a substantially constant width, W1, in the cross direction CD. And the second belt laminate 408 includes an outer longitudinal edge 109a and an inner longitudinal edge 109b that may define a substantially constant width, W2, in the cross direction CD, wherein W2 is greater than W1. It is to be appreciated that in some configurations, W1 may be equal to or greater than W2. As previously mentioned, the first belt laminate 406 is separated in the cross direction CD from the second belt laminate 408 to define a gap between the inner longitudinal edge 107b of the first belt laminate 406 and the inner longitudinal edge 109b of the second belt laminate 408. As discussed in more detail below, the first and second belt laminate 406, 408 advance from the diverter 508 to a nip 316 between the carrier apparatus 308 and a roll 318 to be combined with discrete chassis 102.

In some configurations, the graphics G may be positioned on the continuous elastic laminate 402 such that cutter 506 may cut through graphics G. For example, as shown in FIGS. 4 and 5B, the cutter may 506 may slit the continuous elastic laminate 402 along the machine direction MD through the graphics G, such that a first portion of the of the graphic G remains with the first belt laminate 406, and a second portion of the graphic G remains with the second belt laminate 408. As shown in FIG. 5B, the central zone 500 and the first and second zones 501, 503 extend in the cross direction CD for the entire width W1 of first elastic belt laminate 406 and for the entire width W2 of the second elastic belt laminate 408. It should also be appreciated that the cutter 506 may slit the continuous elastic laminate 402 without cutting graphics G. As such, in some embodiments, the graphics G may remain entirely on the first belt laminate 406 and/or the second belt laminate 408 after the continuous elastic laminate 402 has been slit by cutter 506.

Referring now to FIGS. 4 and 5C, a continuous length of chassis assemblies 302 are advanced in a machine direction MD and define a width in a cross direction CD. The continuous length of chassis assemblies 302 may include absorbent assemblies 140 sandwiched between topsheet material 138 and backsheet material 136, leg elastics, barrier leg cuffs and the like. As shown in FIG. 5C, portion of the chassis assembly is cut- to show a portion of the topsheet material 138 and an absorbent assembly 140. The continuous length of chassis assemblies 302 advance to a carrier apparatus 308 and are cut into discrete chassis 102 with knife roll 306, while advancing in the orientation shown in FIG. 5D1, wherein the longitudinal axis 124 of each chassis 102 is generally parallel with the machine direction MD.

After the discrete absorbent chassis 102 are cut by the knife roll 306, the carrier apparatus 308 rotates and advances the discrete chassis 102 in the machine direction MD in the orientation shown in FIG. 5D1. While the chassis 102 shown in FIG. 5D1 is shown with the second laterally extending end edge 146 as a leading edge and the first laterally extending end edge 144 as the trailing edge, it is to be appreciated that in other embodiments, the chassis 102 may be advanced in other orientations. For example, the chassis may be oriented such that the second laterally extending end edge 146 is a trailing edge and the first laterally extending end edge 144 is a leading edge. The carrier apparatus 308 also rotates while at the same time changing the orientation of the advancing chassis 102. In changing the chassis orientation, the carrier apparatus 308 may turn each chassis 102 such that the lateral axis 126 of the chassis 102 is parallel or generally parallel with the machine direction MD, such as shown in FIG. 5D2. The carrier apparatus 308 may also change the speed at which the chassis 102 advances in the machine direction MD to a different speed. FIG. 5D2 shows the orientation of the chassis 102 on the carrier apparatus 308 while advancing in the machine direction MD. More particularly, FIG. 5D2 shows the chassis 102 with the lateral axis 126 of the chassis 102 generally parallel with the machine direction MD, and wherein the second longitudinal side edge 130 is the leading edge and the first longitudinal side edge 128 is the trailing edge. It is to be appreciated that various forms of carrier apparatuses may be used with the methods herein, such as for example, the carrier apparatuses disclosed in U.S. Pat. No. 7,587,966 and U.S. Patent Publication Nos. 2013/0270065 A1; 2013/0270069 A1; 2013/0270066 A1; and 2013/0270067 A1. In some embodiments, the carrier apparatus 308 may rotate at a variable angular velocity that may be changed or adjusted by a controller in order to change the relative placement of the chassis 102 and the advancing belt laminates 406, 408.

As discussed below with reference to FIGS. 4, 5E, 5F, and 5G, the chassis 102 are transferred from the carrier apparatus 308 and combined with advancing, continuous lengths of belt laminates 406, 408, which are subsequently cut to form first and second elastic belts 106, 108 on diapers 100.

Figure 5E:
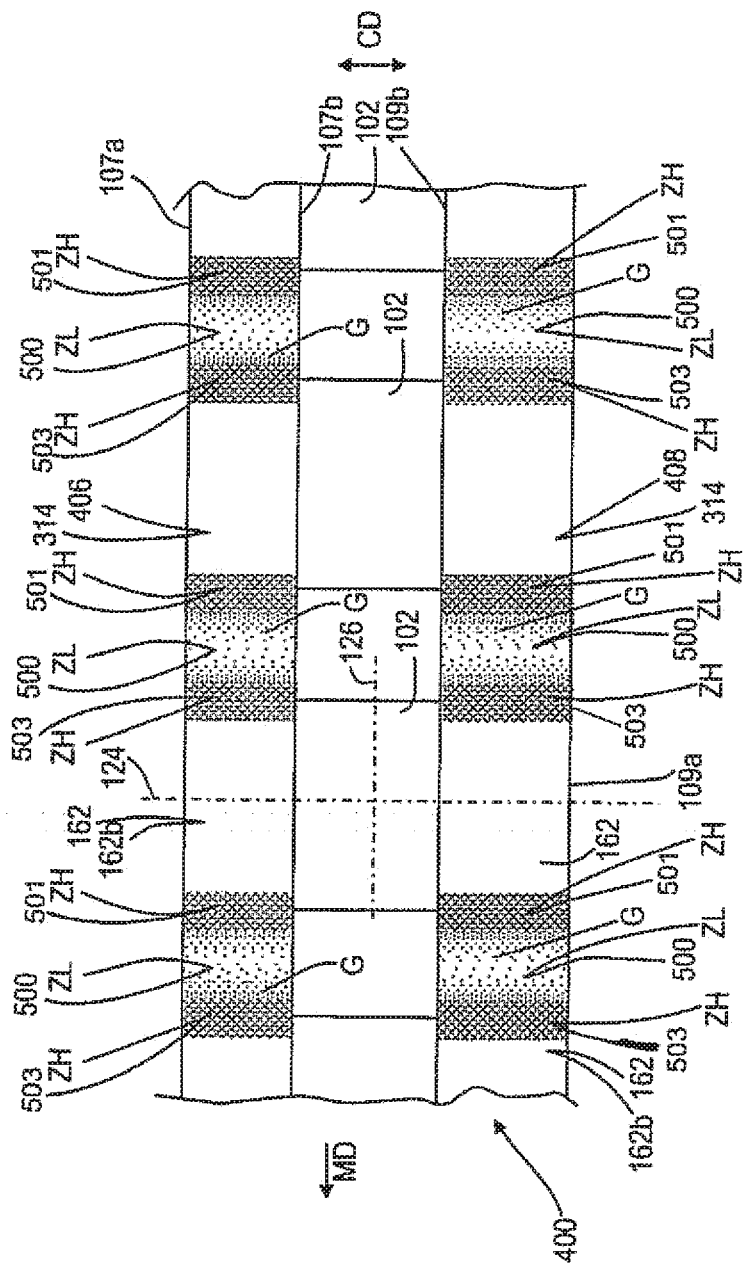
FIG. 5E is a view of multiple discrete chassis spaced from each other along the machine direction MD and connected with each other by the first and second elastic belt laminates from FIG. 4 taken along line E-E.

As shown in FIGS. 4, 5B, and 5E, the chassis 102 are transferred from the carrier apparatus 308 to a nip 316 between the carrier apparatus 308 and a roll 318 where the chassis 102 is combined with continuous lengths of advancing front belt 406 and back belt 408 substrate material. The front belt laminate material 406 and the back belt laminate material 408 each include a wearer facing surface 312 and an opposing garment facing surface 314. As such, the second surface 162b of the outer layer belt substrate 162 may define the garment facing surface 314, and the second surface 164b of the inner layer belt substrate 164 may define the wearer facing surface 312. The wearer facing surface 312 of the first belt laminate 406 may be combined with the garment facing surface 134 of the chassis 102 along the first waist region 116, and the wearer facing surface 312 of the second belt laminate 408 may be combined with the garment facing surface 134 of the chassis 102 along the second waist region 118. As shown in FIG. 4, adhesive 320 may be intermittently applied to the wearer facing surface 312 of the first and second belt laminates 406, 408 before combining with the discrete chassis 102 at the nip 316 between roll 318 and the carrier apparatus 308.

With continued reference to FIGS. 4 and 5E, a continuous length of absorbent articles 400 are defined by multiple discrete chassis 102 spaced from each other along the machine direction MD and connected with each other by the second belt laminate 408 and the first belt laminate 406. As shown in FIG. 4, the continuous length of absorbent articles 400 advances from the nip 316 to a folding apparatus 332. At the folding apparatus 332, each chassis 102 is folded in the cross direction CD parallel to or along a lateral axis 126 to place the first waist region 116, and specifically, the inner, body facing surface 132 into a facing, surface to surface orientation with the inner, body surface 132 of the second waist region 118. The folding of the chassis also positions the wearer facing surface 312 of the second belt laminate 408 extending between each chassis 102 in a facing relationship with the wearer facing surface 312 of the first belt laminate 406 extending between each chassis 102.

As shown in FIGS. 4 and 5F, the folded discrete chassis 102 connected with the first and second belt laminates 406, 408 are advanced from the folding apparatus 332 to a bonder apparatus 334. The bonder apparatus 334 operates to bond an overlap area 362, thus creating discrete bonds 336a, 336b. The overlap area 362 includes a portion of the second belt laminate 408 extending between each chassis 102 and a portion of the first belt laminate 406 extending between each chassis 102. As shown in FIG. 5F, the discrete bonds 336a, 336b are positioned in the central zone 500 of each graphic G. As previously mentioned, the central zone 500 is a low intensity zone ZL. As such, the placement of the discrete bonds 336a, 336b in the central zone 500 may help reduce noticeable visible results of imprecise and/or inconsistent placement of the discrete bonds. It is to be appreciated that the bonder apparatus 334 may be configured in various ways to create bonds 336a, 336b in various ways, such as for example with heat, adhesives, pressure, and/or ultrasonics. It is also to be appreciated that in some embodiments, the apparatus 300 may also be configured to refastenably bond the overlap area 362, in addition to or as opposed to permanently bonding the overlap area 362. Thus, the discrete bonds 336a, 336b may be configured to be refastenable, such as with hooks and loops, and may be positioned in the central zone 500 of each graphic G.

Referring now to FIGS. 4 and 5G, the continuous length of absorbent articles 400 are advanced from the bonder 334 to a cutting apparatus 338 where the first belt laminate 406 and the second belt laminate 408 are cut along the cross direction CD through the central zones 500 of each graphic G and between adjacent bonds 336a, 336b to create discrete absorbent articles 100. Because the central zone 500 is a low intensity zone ZL, cutting through central zone 500 with cutting apparatus 338 may help reduce noticeable visible results of imprecise and/or inconsistent placement of the cut lines.

As shown in FIG. 5G, the first belt laminate 406 and the second belt laminate 408 are cut into discrete pieces to form the front and back elastic belts 106, 108, each having a pitch length, PL, extending along the machine direction. As such, bond 336a may correspond with and form a first side seam 178 on an absorbent article 100, and the bond 336b may correspond with and form a second side seam 180 on a subsequently advancing absorbent article. In addition, the cutting apparatus 338 severs the first belt laminate 406 and the second belt laminate 408 through the low intensity zones ZL of the graphics G to define the first graphic G1 adjacent the first side seam 178 and the second graphic G2 adjacent the second side seam 180. As such, the first graphic G1 may be defined by the second zone 503 and a portion of the central zone 500 of a graphic G, and the second graphic G2 may be defined by the first zone 501 and another portion of the central zone 500 of a graphic G.

Figure 6A:
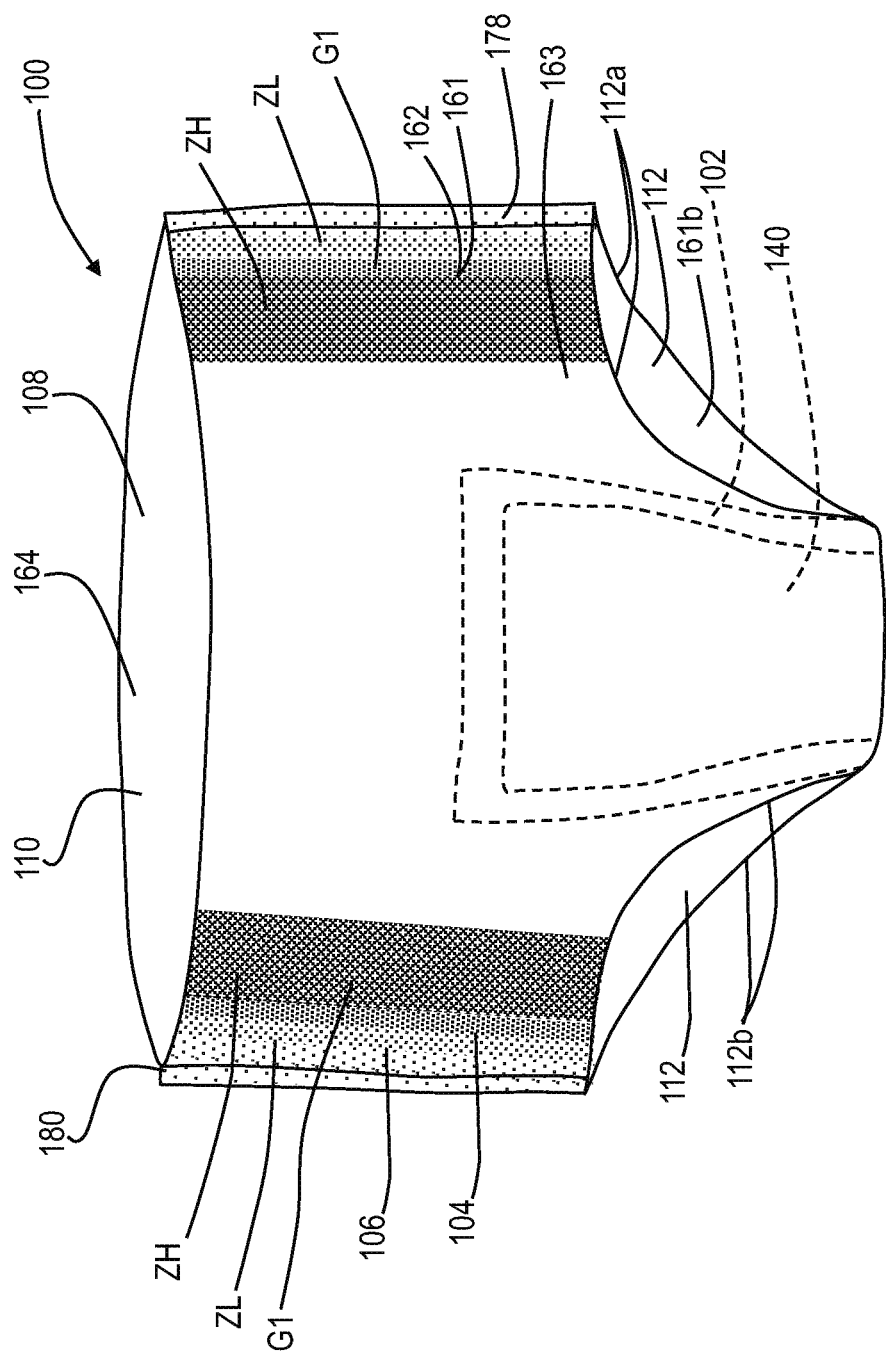
FIG. 6A is a front perspective view of a diaper pant constructed with a contiguous outer cover.

It is to be appreciated that the processes and apparatuses herein may be configured to manufacture various types of diaper pants having the graphics G discussed above. In some embodiments, the diaper pants 100 may include a chassis 102 and elastic belts 106, 108 configured in different ways other than as depicted in FIGS. 1A-2B. For example, FIGS. 6A-7 show a diaper pant 100 having many of the same components as described above with reference to FIGS. 1A-2B, except the outer layer 162 of the elastic belts 106, 108 is configured as a contiguous outer cover 161 that extends through the first waist region 116, crotch region 119, and second waist region 118. Thus, as shown in FIG. 7, the outer cover 161 also includes a first waist end region 116, a crotch region 119, and an opposing second waist end region 118. The outer cover 161 also includes a garment facing surface 162b and an opposing wearer facing surface 162a. As such, elastic members 168 of the elastic belts 106, 108 may be connected with the wearer facing surface 162a of the outer cover 161. And the chassis 102 may be positioned on the wearer facing surface 162a of the outer cover 161. As such, the backsheet 136 may include a portion of the outer cover 161. In addition, the outer cover 161 may include a first longitudinal side edge 128a and a second longitudinal side edge 130a that are positioned laterally outboard the first longitudinal side edge 128 of the chassis 102 and second longitudinal side edge 130 of the chassis 102, respectively, as shown in FIG. 7. As shown in FIG. 6A, the first longitudinal side edge 128a may define the perimeter 112a of one leg opening 112, and the second longitudinal side edge 130a may define the perimeter 112b of the other leg opening 112. It is to be appreciated also that the first longitudinal side edge 128a and a second longitudinal side edge 130a may aligned with or positioned laterally inboard of the first longitudinal side edge 128 of the chassis 102 and second longitudinal side edge 130 of the chassis 102, respectively. As such, in some embodiments, the perimeter 112a of one leg opening 112 may be defined by portions of the first longitudinal edges 128, 128a, and the perimeter 112b of the other leg opening may be defined by portions of the second longitudinal edges 130, 130a.

Figure 6B:
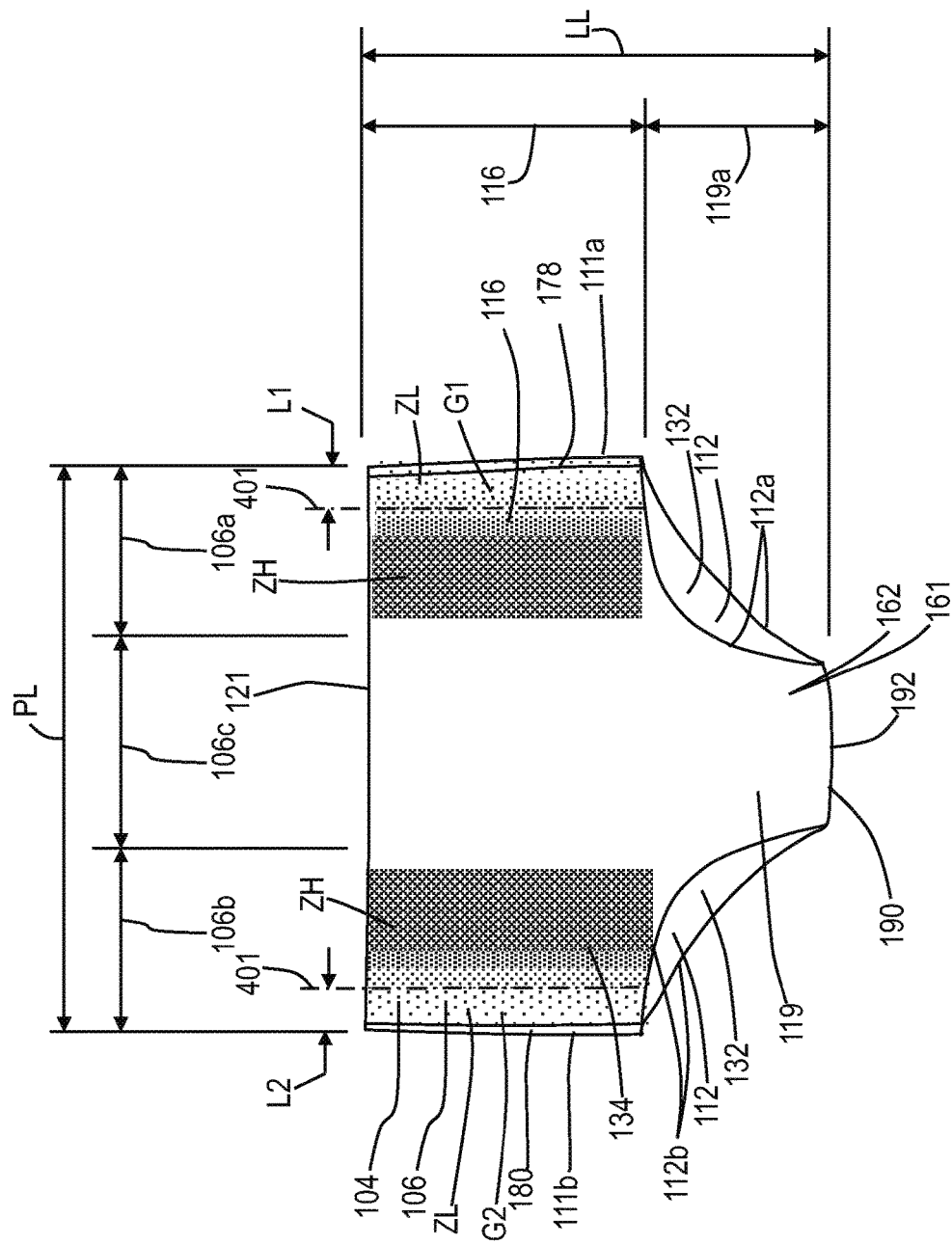
FIG. 6B is a front plan view of the diaper pant of FIG. 6A.

FIG. 6B shows a front plan view of a diaper pant 100 in a laid flat condition illustrating various regions of the diaper pant 100. And 6C shows a rear plan view of the diaper pant 100 in a laid flat condition illustrating various regions of the diaper pant 100. As discussed above, the diaper pant 100 defines include an inner, body facing surface 132, and an outer, garment facing surface 134. The diaper pant 100 also includes a crotch end 190 that is defined by a lateral fold line 192 in the crotch region 119. As such, the lateral fold line 192 divides the crotch region into a first crotch region 119a and a second crotch region 119b.

The diaper pant 100 is shown in FIGS. 6A-6C as having a first elastic belt 106, and a second elastic belt 108. The first belt 106 has a first end region 106a, an opposing second end region 106b, and a central region 106c. And the second belt 108 has a first end region 108a, an opposing second end region 108b, and a central region 108c. The first end regions 106a, 108a are connected together at a first side seam 178, and the second end regions are 106b, 108b are connected together at a second side seam 180. As shown in FIGS. 6B and 6C, the distance between the first longitudinal side edge 111a and the second longitudinal side edge 111b defines the pitch length, PL, of the first elastic belt 106, and the distance between the first longitudinal side edge 113a and the second longitudinal side edge 113b defines the pitch length, PL, of the second elastic belt 108.

The first end region 106a the first belt 106 may extend approximately 20% to 40% of the pitch length PL of the diaper pant 100 in an assembled, laid-flat, relaxed condition, and the first end region 108a the second belt 108 may extend approximately 20% to 40% of the pitch length PL of the diaper pant 100 in an assembled, laid-flat, relaxed condition. The second end region 106b the first belt 106 may extend approximately 20% to 40% of the pitch length PL of the diaper pant 100 in an assembled, laid-flat, relaxed condition, and the second end region 108b the second belt 108 may extend approximately 20% to 40% of the pitch length of the diaper pant 100 in an assembled, laid-flat, relaxed condition. The central region 106c the first belt 106 may extend approximately 20% to 60% of the pitch length PL of the diaper pant 100 in an assembled, laid-flat, relaxed condition, and the central region 108c the second belt 108 may extend approximately 20% to 60% of the pitch length PL of the diaper pant 100 in an assembled, laid-flat, relaxed condition.

The diaper pant 100 in FIGS. 6B and 6C is also shown as having a longitudinal length LL that is defined by the distance between the first waist edge 121 and the crotch end 190 (or the lateral fold line 192), or if longer, the distance from the second waist edge 122 to the crotch end 190 (or the lateral fold line 192). The longitudinal length LL may be measured along the longitudinal centerline 124 of the diaper pant 100. As shown in FIGS. 6B-6C, the first waist region 116 extends a distance generally in the longitudinal direction from the waist edge 121 along the side seams 178, 180 to the leg openings 112, and the second waist region 118 extends a distance generally in the longitudinal direction from the waist edge 122 along the side seams 178, 180 to the leg openings 112. Hence, a first crotch region 119a extends a distance from the crotch end 190 to the first waist region 116, and a second crotch region 119b extends a distance from the crotch end 190 to the second waist region 118. In some embodiments, the first waist region 116 and/or the second waist region 118 may extend about two-thirds the longitudinal length LL of the assembled diaper pant 100. In addition, the first crotch region 119a and/or the second crotch region 119b may extend about one-third the longitudinal length LL of the assembled diaper pant 100.

The diaper pant 100 shown in FIGS. 6A-6C also includes printed graphics G1, G2 on the first elastic belt 106 and the second elastic belt 108, wherein each graphic includes a high intensity zone ZH and a low intensity zone ZL. As shown in FIGS. 6B-6C, the low intensity zones ZL are positioned in the opposing end regions 106a, 106b of the first belt 106 as well as the opposing end regions of 108a, 108b of the second belt 108. As discussed above with other embodiments, the end regions of the belts 106, 108 where the low intensity zones ZL are located, may be subject to cutting and seaming process operations during the assembly process. In addition, the high intensity zones ZH are positioned relatively closer to the central regions 106c, 108c of the first and second belts 106, 108.

With continued reference to FIGS. 6B-6C, the low intensity zone ZL of the graphic G1 on the front belt 106 is positioned between the high intensity zone ZH and the first longitudinal side edge 111a, and the low intensity zone ZL of the graphic G2 on the front belt 106 is positioned between the high intensity zone ZH and the second longitudinal side edge 111b. For the purposes of clarity, dashed lines 401 are shown to represent example boundaries between the high intensity zones ZH and the low intensity zones ZL. It is to be appreciated that such boundaries between the high intensity zones ZH and the low intensity zones ZL can also be curved, angled, and/or straight. It is to be appreciated that the low intensity zone ZL of the graphic G1 on the front belt 106 may extend from the high intensity zone ZH entirely to the first longitudinal side edge 111a, and the low intensity zone ZL of the graphic G2 on the front belt 106 may extend from the high intensity zone ZH entirely to the second longitudinal side edge 111b. It is to be appreciated that in some embodiments, the low intensity zones ZL may not extend all the way to the first and second edges 111a, 111b.

As also shown in FIGS. 6A-6C, the low intensity zones ZL of the graphic G1 and graphic G2 on the front belt 106 may extend entirely from the outer laterally extending waist edges 121, 122 to perimeters of the leg openings 112. It is to be appreciated that in some embodiments, the low intensity zones ZL may not extend all the way to one of or both of the waist edges 121, 122 and/or the leg openings 112.

As shown in FIGS. 6B-6C, the low intensity zone ZL of the first graphic G1 may define a length L1 along the first belt 106 and the second belt 108, and the low intensity zone ZL of the second graphic G2 may define a length L2 along the first belt 106 and the second belt 108. It is to be appreciated that lengths L1, L2 of the low intensity zones ZL may vary. In some embodiments, the lengths L1 and/or L2 may be from about 5 mm to about 30 mm. In some embodiments, the lengths L1, L2 may be expressed in terms relative to the pitch lengths PL of the first and second belts 106, 108. For example, in some embodiments, the pitch lengths PL of the first and/or second belts 106, 108 may be about 20 to about 50 times the lengths L1 and/or L2.

Figure 8:
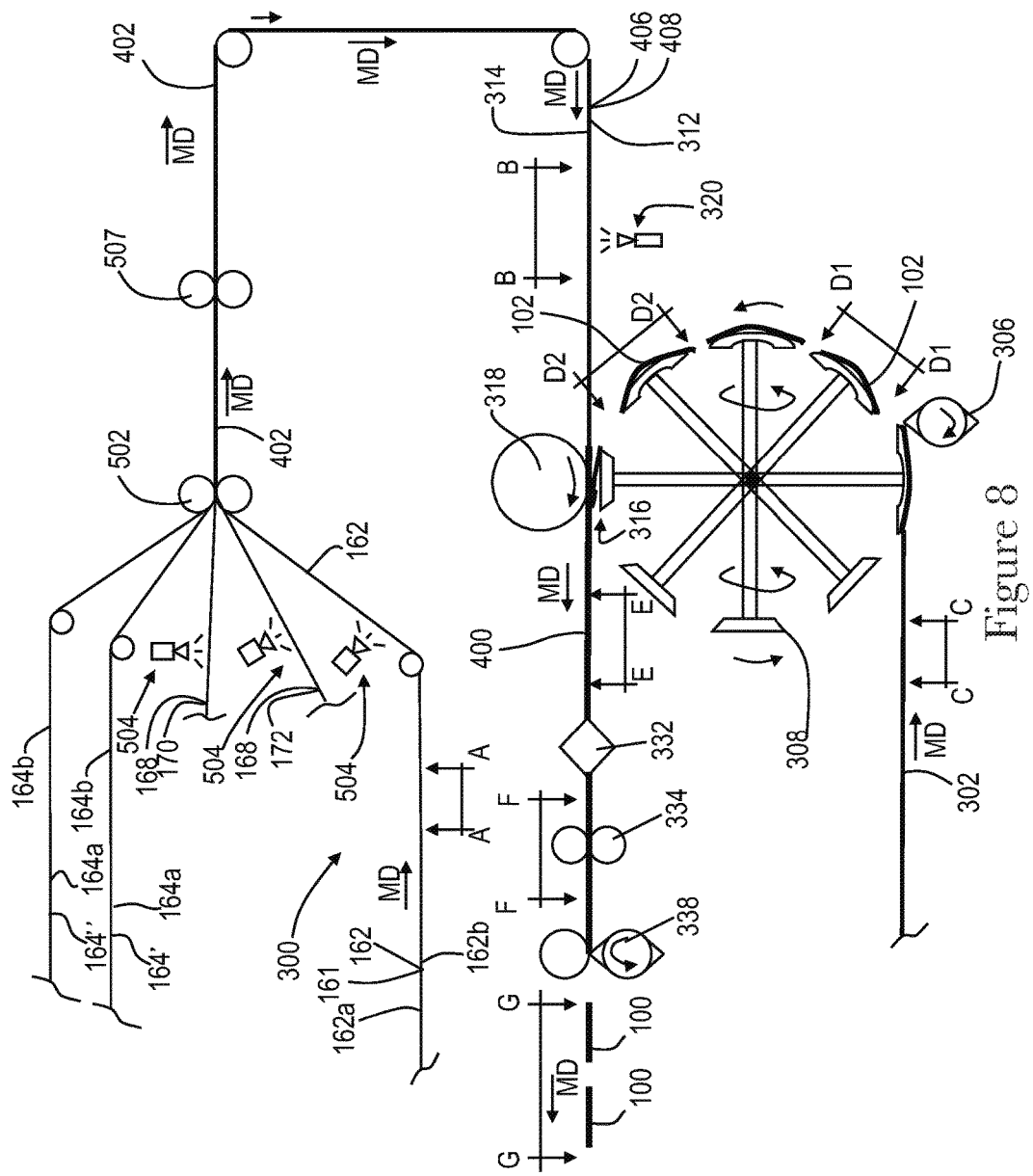
FIG. 8 is a schematic side view of a converting apparatus adapted to manufacture pre-fastened, pant diapers.
Figure 9A:
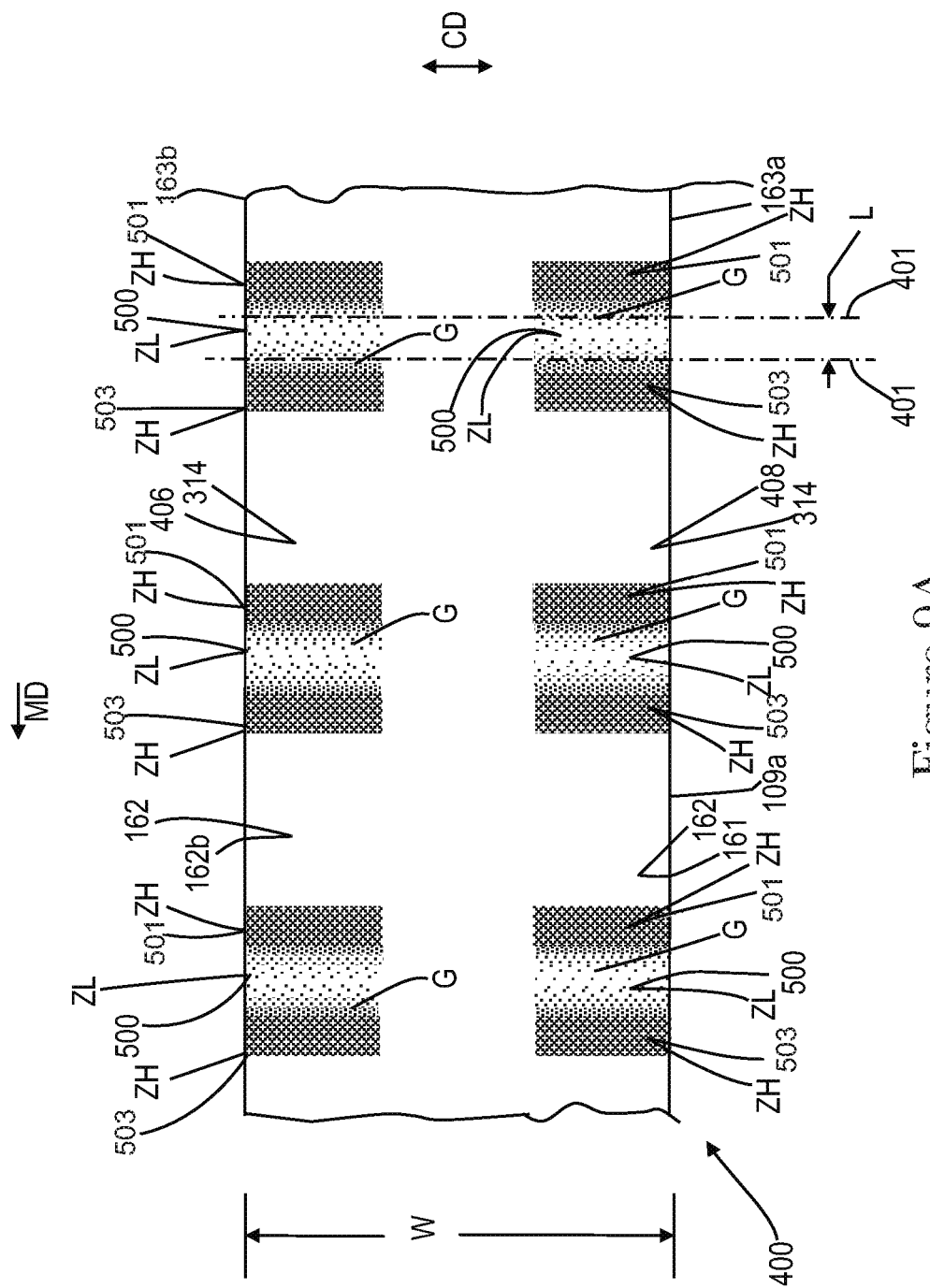
FIG. 9A is a view of a continuous length of an advancing first substrate from FIG. 8 taken along line A-A.
Figure 9B:
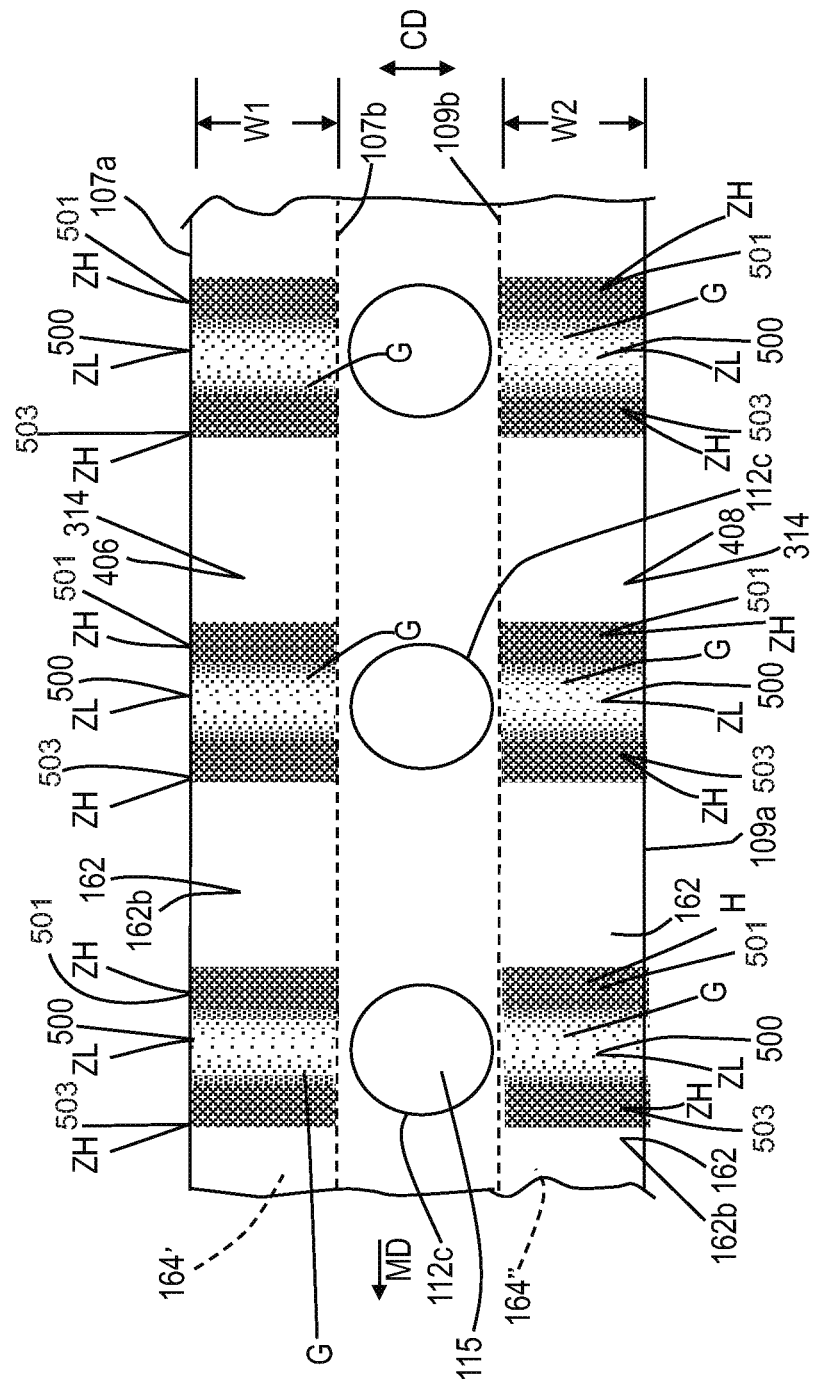
FIG. 9B is a view of continuous lengths of advancing first and second elastic belt laminates from FIG. 8 taken along line B-B.

As discussed above, substrates and/or components that may be incorporated into manufactured absorbent articles, such as shown in FIGS. 6A-7, may include graphics positioned and/or printed in such a manner so as to reduce noticeable visible results of imprecise and/or inconsistent manufacturing operations performed in areas where the printing is located. And FIG. 8 shows a converting apparatus 300 configured to assemble diaper pants such as shown in FIGS. 6A-7. As shown in FIG. 8, a first continuous substrate layer in the form of a continuous length of outer layer belt substrate 162 is combined with first and second separate continuous lengths of inner layer belt substrates 164', 164" and elastics 168 form a continuous elastic laminate 402. The outer layer belt substrate 162 also defines the outer cover 161 discussed above with reference to FIGS. 6A-7. With reference to FIGS. 8, 9A, and 9B, continuous lengths of outer layer belt substrate 162, first and second inner layers of belt substrate 164', 164", outer elastic strands 170 and inner elastic strands 172 are advanced in a machine direction MD and combined at nip rolls 502 to form the continuous elastic laminate 402.

Before entering the nip rolls 502, the outer layer belt substrate 162 and/or the first and second inner belt substrates 164', 164" may be printed with graphics having high intensity zones and low intensity zones as discussed above. It is to be appreciated that the graphic printing may be done during the assembly process and/or may done separate to the assembly process, such as for example, printing the substrates off line where the printed substrates may be stored until needed for production.

As shown in FIGS. 8 and 9A, the outer belt substrate 162 includes first surface 162a and an opposing second surface 162b, and defines a width W in the cross direction between opposing longitudinal edges 163a, 163b. And the outer belt substrate 162 may advance in the machine direction and may include graphics G printed on the first surface 162a of the outer layer belt substrate 162. As shown in FIG. 9A, although the graphics G are printed on the first surface 162a of the outer layer belt substrate 162, the graphics G may be visible through the second surface 162b. It is also to be appreciated that the graphics G may be printed on either or both the first and second surfaces 162a, 162b of the outer belt substrate 162. It is also to be appreciated that graphics may be printed on either or both the first and second surfaces 164a, 164b of the first and second inner belt substrates 164', 164".

As shown in FIG. 9A, each graphic G extends in the machine direction and includes a central zone 500 positioned between longitudinally opposing first and second zones 501, 503. The central zone 500 is a low intensity zone ZL and the first and second zones 501, 503 are high intensity zones ZH. For the purposes of clarity, dashed lines 401 are shown in FIG. 9A to represent example boundaries between the high intensity zones ZH and the low intensity zones ZL. It is to be appreciated that such boundaries between the high intensity zones ZH and the low intensity zones ZL can also be curved, angled, and/or straight. As shown in FIG. 9A, the central zone 500 defines a length, L, in the machine direction MD. It is to be appreciated that lengths L of the central zones 500 may vary. In some embodiments, the lengths L may be from about 10 to about 60 mm. In some embodiments, the lengths L may also be expressed in terms relative to the pitch lengths PL of the first and second belts 106, 108 of the assembled diapers 100. For example, in some embodiments, the pitch lengths PL of the first and/or second belts 106, 108 may be about 10 to about 25 times the length L. In addition, the central zone 500 and the first and second zones extend in the cross direction CD for the entire width W of the outer belt substrate 162. It is to be appreciated that in some embodiments, the central zone 500 and/or the first and second zones may extend in the cross direction CD for less than the entire width W. Although FIG. 9A depicts consecutive first and second zones 501, 503 as being separate from each other, it is to be appreciated that the graphics G may be printed such that the consecutive first and second zones may be contiguous, such as discussed above with reference to FIG. 5A1.

Referring back to FIG. 8, before entering the nip rolls 502, the outer elastic strands 170 and inner elastic strands 172 are stretched in the machine direction MD. In addition, adhesive 504 may applied to the elastic strands 170, 172 as well as either or both of the continuous lengths of outer layer belt substrate 162 and inner layer belt substrates 164', 164" before entering nip rolls 502. As such, the elastic strands 168 are bonded between the first surface 162a of the outer layer belt substrate 162 and the first surfaces 164a of inner layer belt substrates 164', 164" at the nip rolls 502. Further, adhesive 504 may be applied intermittently along the lengths of the inner elastic strands 172 and/or intermittently along the length of either or both of the continuous lengths of outer layer belt substrate 162 and inner layer belt substrates 164', 164" before entering nip rolls 502. As previously discussed, the inner elastic strands 172 may be intermittently bonded to either or both of the continuous lengths of outer layer belt substrate 162 and inner layer belt substrates 164', 164" along the machine direction MD.

With continued reference to FIG. 8, from the nip rolls 502 the continuous elastic laminate 402 advances in the machine direction MD to a cutter 507 that removes material from a central region of the continuous elastic laminate 402 to form holes 115 defined by perimeter edges 112c, such as shown in FIG. 9B. The perimeter edges 112c may define all or portions of the perimeters 112a, 112b of the leg openings 112 mentioned above and shown in FIG. 6A. It is to be appreciated that the cutter may be configured to remove material from only the outer layer belt substrate 162. In some configurations, the cutter 507 may be configured to remove material from the outer belt substrate 162 as well as the first inner layer belt substrate 164' and/or second inner layer belt substrate 164". The cutter 507 may also be configured as a perforator that perforates the belt material with a line of weakness and wherein the belt material is separated along the line of weakness in a later step. It is also to be appreciated that the cutter 507 may be configured to form holes 115 in the continuous elastic laminate 402 before or after the continuous elastic laminate 402 is combined with the chassis 102.

As shown in FIG. 9B, the continuous elastic laminate 402 includes a first elastic belt laminate 406 and a second elastic belt laminate 408. More particularly, the combination of the outer layer belt substrate 162, the first inner layer of belt substrate 164', and elastic strands 168 defines the first belt laminate 406. And the combination of the outer layer belt substrate 162, the second inner layer of belt substrate 164", and elastic strands 168 defines the second belt laminate 408. The first belt laminate 406 includes an outer longitudinal edge 107a and an inner longitudinal edge 107b that may define a substantially constant width, W1, in the cross direction CD. And the second belt laminate 408 includes an outer longitudinal edge 109a and an inner longitudinal edge 109b that may define a substantially constant width, W2, in the cross direction CD. In some configurations, W2 equal to W1. It is also to be appreciated that in some configurations, W1 may be less than or greater than W2. The first belt laminate 406 is separated in the cross direction from the second belt laminate 408 to define a gap between the inner longitudinal edge 107b of the first belt laminate 406 and the inner longitudinal edge 109b of the second belt laminate 408.

As discussed above with reference to FIGS. 4, 5C, 5D1, and 5D2, and as shown in FIG. 8, a continuous length of chassis assemblies 302 are advanced in a machine direction MD to a carrier apparatus 308 and are cut into discrete chassis 102 with knife roll 306, while advancing in the orientation shown in FIG. 5D1. After the discrete absorbent chassis 102 are cut by the knife roll 306, the carrier apparatus 308 rotates and advances the discrete chassis 102 in the machine direction MD in the orientation shown in FIG. 5D1. The carrier apparatus 308 also rotates while at the same time changing the orientation of the advancing chassis 102. In changing the chassis orientation, the carrier apparatus 308 may turn each chassis 102 such that the lateral axis 126 of the chassis 102 is parallel or generally parallel with the machine direction MD, such as shown in FIG. 5D2.

Figure 9E:
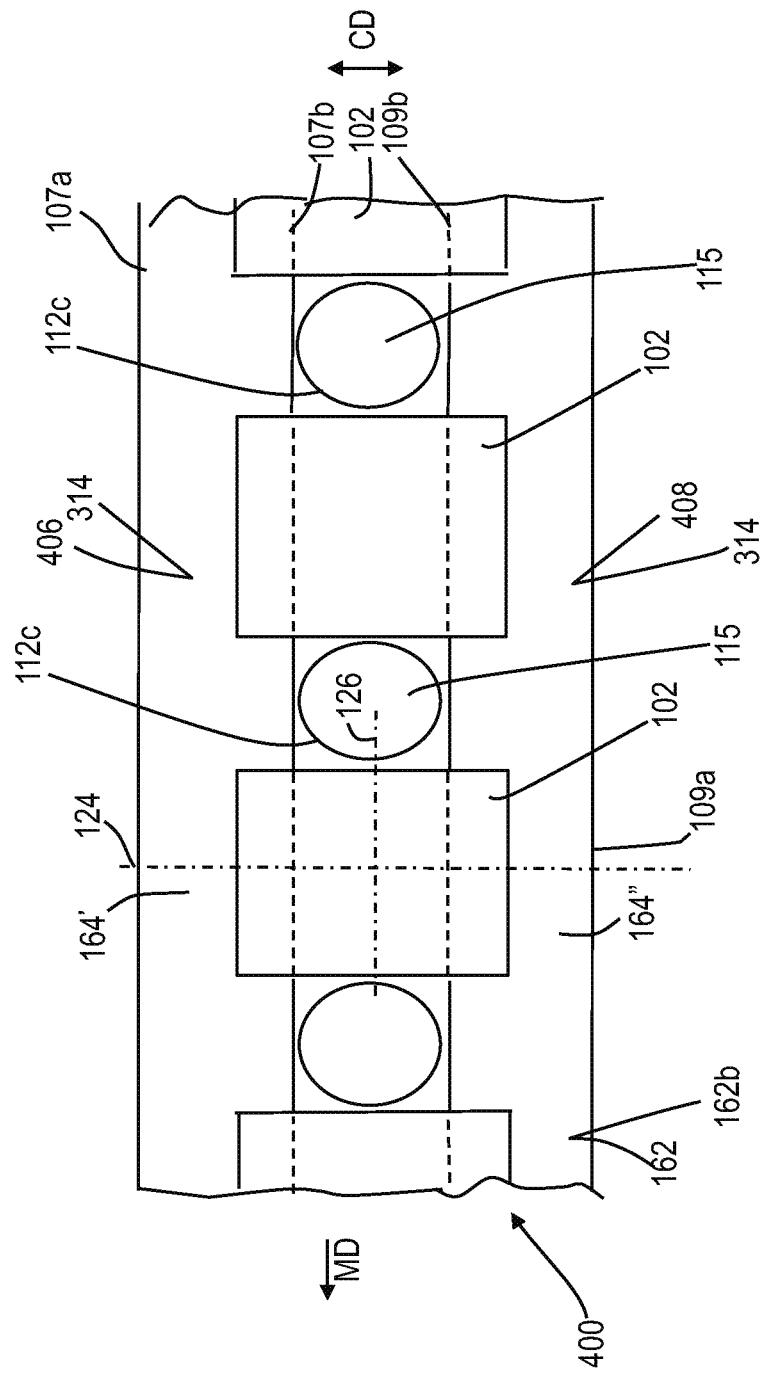
FIG. 9E is a view of multiple discrete chassis spaced from each other along the machine direction MD and connected with each other by the first and second elastic belt laminates from FIG. 8 taken along line E-E.

As shown in FIGS. 8 and 9E, the chassis 102 are transferred from the carrier apparatus 308 to a nip 316 between the carrier apparatus 308 and a roll 318 where the chassis 102 is combined with the continuous elastic laminate 402. The chassis 102 may be spaced apart from each other along the machine direction MD on the continuous elastic laminate 402, wherein at least one hole 115 is positioned between two consecutive chassis 102. The continuous elastic laminate 402 includes a wearer facing surface 312 and an opposing garment facing surface 314. As such, the second surface 162b of the outer layer belt substrate 162 may define the garment facing surface 314. And the first surface 162a of the outer layer belt substrate 162 and the second surfaces 164b of the inner layer belt substrates 164', 164" may define the wearer facing surface 312. The wearer facing surface 312 of the continuous elastic laminate 402 may be combined with the garment facing surface 134 of the chassis 102. As shown in FIG. 8, adhesive 320 may be intermittently applied to the wearer facing surface 312 of the continuous elastic laminate 402 before combining with the discrete chassis 102 at the nip 316 between roll 318 and the carrier apparatus 308.

With continued reference to FIGS. 8 and 9E, a continuous length of absorbent articles 400 are defined by multiple discrete chassis 102 spaced from each other along the machine direction MD and connected with each other by the continuous elastic laminate 402. As shown in FIG. 8, the continuous length of absorbent articles 400 advances from the nip 316 to a folding apparatus 332. At the folding apparatus 332, the continuous elastic laminate 402 and each chassis 102 are folded in the cross direction CD parallel to or along a lateral axis 126 to place the first waist region 116, and specifically, the inner, body facing surface 132 into a facing, surface to surface orientation with the inner, body surface 132 of the second waist region 118. The folding operation creates the lateral fold line 192 that defines the crotch end 190 discussed above with reference to FIGS. 6B and 6C. The folding of the chassis also positions the wearer facing surface 312 of the second belt laminate 408 extending between each chassis 102 in a facing relationship with the wearer facing surface 312 of the first belt laminate 406 extending between each chassis 102.

As shown in FIGS. 8 and 9F, the folded continuous length of absorbent articles 400 are advanced from the folding apparatus 332 to a bonder apparatus 334. The bonder apparatus 334 operates to bond an overlap area 362, thus creating discrete bonds 336a, 336b. The overlap area 362 includes a portion of the second belt laminate 408 extending between each chassis 102 and a portion of the first belt laminate 406 extending between each chassis 102. As shown in FIG. 5F, the discrete bonds 336a, 336b are positioned in the central zone 500 of each graphic G. As previously mentioned, the central zone 500 is a low intensity zone ZL. As such, the placement of the discrete bonds 336a, 336b in the central zone 500 may help reduce noticeable visible results of imprecise and/or inconsistent placement of the discrete bonds. It is to be appreciated that the bonder apparatus 334 may be configured in various ways to create bonds 336a, 336b in various ways, such as for example with heat, adhesives, pressure, and/or ultrasonics. It is also to be appreciated that in some embodiments, the apparatus 300 may be configured to refastenably bond the overlap area 362, in addition to or as opposed to permanently bonding the overlap area 362. Thus, the discrete bonds 336a, 336b may be configured to be refastenable, such as with hooks and loops, and may be positioned in the central zone 500 of each graphic G.

Referring now to FIGS. 8 and 9G, the continuous length of absorbent articles 400 are advanced from the bonder 334 to a cutting apparatus 338 where the first belt laminate 406 and the second belt laminate 408 are cut along the cross direction CD through the central zones 500 of each graphic G and between adjacent bonds 336a, 336b to create discrete absorbent articles 100. Because the central zone 500 is a low intensity zone ZL, cutting through central zone 500 with cutting apparatus 338 may help reduce noticeable visible results of imprecise and/or inconsistent placement of the cut lines.

As shown in FIG. 9G, the continuous length of absorbent articles 400 are cut into discrete pieces to form the front and back elastic belts 106, 108, each having a pitch length, PL, extending along the machine direction. As such, bond 336a may correspond with and form a first side seam 178 on an absorbent article 100, and the bond 336b may correspond with and form a second side seam 180 on a subsequently advancing absorbent article. In addition, the cutting apparatus 338 severs the first belt laminate 406 and the second belt laminate 408 through the graphics G to define the first graphic G1 adjacent the first side seam 178 and the second graphic G2 adjacent the second side seam 180. As such, the first graphic G1 may be defined by the second zone 503 and a portion of the central zone 500 of a graphic G, and the second graphic G2 may be defined by the first zone 501 and another portion of the central zone 500 of a graphic G.

Method for Measuring Print Color and Print Density

Print color and density on a printed nonwoven or film is measured using a hand held, 45°/0° configuration, hemispherical geometry spectrophotometer, the X-rite eXact Spectrophotometer (available from X-Rite, Grand Rapids Mich.), or equivalent instrument, with a 4.0 mm optical aperture. This instrument measures print density based on reflection density expressed as the logarithm of the reciprocal of the reflectance factor. Set the scale to L*a*b* units, 2° Observer, C Illumination, Abs White Base, no Physical Filter, and the Density Standard of ANSI T. Measurements are performed in an environment controlled lab held at about 23° C.±2 C.° and 50%±2% relative humidity.

Calibrate the instrument per the vender's instructions using the standard white board (available as PG2000 from Sun Chemical-Vivitek Division, Charlotte, N.C.) each day before analyses are performed. Remove the substrate to be measured from the sample article. If necessary, a cryogenic freeze-spray (e.g., Cyto-freeze, available from Control Company, Houston Tex.) can be used to facilitate removal. Samples are conditioned at about 23° C.±2 C.° and 50%±2% relative humidity for 2 hours before testing.

Place the Standard White Board on a horizontal bench, standard side facing upward. Place the specimen flat on top of the Standard White Board with the printed side facing upward. Place the eXact spectrophotometer on the specimen such that the measurement site is free of folds and wrinkles and 100% of the measurement site is within the instrument's aperture. Take a reading for density and L*a*b* color and record each to the nearest 0.01 units.

In like fashion the measure is repeated on corresponding sites on five (5) substantially similar printed substrates and the density and L*a*b* color values averaged separately and reported to the nearest 0.01 units.

It is to be appreciated that the methods of assembly of diaper pants specifically described herein and illustrated in the accompanying drawings are non-limiting example embodiments. The features illustrated or described in connection with one non-limiting embodiment may be combined with the features of other non-limiting embodiments. Such modifications and variations are intended to be included within the scope of the present disclosure.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for assembling disposable diaper pants, each diaper pant comprising a chassis having a first end region and an opposing second end region separated from each other by a central region, and having a longitudinal axis and a lateral axis, the chassis comprising: a topsheet, a backsheet, and an absorbent core disposed between the topsheet and the backsheet, the method comprising the steps of:

advancing a first continuous elastic laminate in a machine direction, the first continuous elastic laminate having an outer longitudinal edge and an inner longitudinal edge;

printing a substrate of the first continuous elastic laminate to form a graphic extending in the machine direction and comprising a central zone positioned between longitudinally opposing first and second zones, wherein each zone comprises a maximum print density, wherein the maximum print density of the central zone is less than or equal to about 30% of the maximum print densities of the first and second zones, and wherein the central zone defines a length, L, in the machine direction;

advancing a second continuous elastic laminate in the machine direction, the second continuous elastic laminate having an outer longitudinal edge and an inner longitudinal edge, wherein the first continuous elastic laminate is separated in a cross direction from the second continuous elastic laminate to define a gap between the inner longitudinal edge of the first continuous elastic laminate and the inner longitudinal edge of the second continuous elastic laminate;

depositing a plurality of chassis spaced apart from each other along the machine direction across the gap and onto the first continuous elastic laminate and the second continuous elastic laminate;

folding each chassis along the lateral axis to position the first continuous elastic laminate into a facing relationship with the second continuous elastic laminate; and cutting the first and second continuous elastic laminates in the cross direction through the central zone of the graphic and into discrete pieces having a pitch length, PL, extending in the machine direction, wherein the pitch length PL is about 10 or more times the length L of the central zone.

2. The method of claim 1, wherein the PL is about 300 mm to about 1000 mm.

3. The method of claim 1, wherein the maximum print density of the first zone is about 0.5.

4. The method of claim 1, wherein the pitch length PL is about 25 or more times the length L of the central zone.

5. The method of claim 1, wherein the central zone extends an entire width of the first elastic laminate in the cross direction.

6. The method of claim 1, further comprising the step of bonding the first continuous elastic laminate with the second continuous elastic laminate at pairs of discrete bond regions separated from each other along the machine direction.

7. The method of claim 6, wherein the step of bonding further comprises refastenably bonding the first continuous elastic laminate with the second continuous elastic laminate.

8. The method of claim 6, wherein the pairs of discrete bond regions are positioned in the central zones.

9. The method of claim 1, wherein the first zone comprises a first design and the second zone comprises a second design that is different from the first design.

10. The method of claim 1, further comprising the steps of:

advancing a first continuous substrate having a first surface and an opposing second surface in the machine direction;

advancing a second continuous substrate having a first surface and an opposing second surface in the machine direction;

bonding elastic strands in a stretched state between the first surface of the first continuous substrate and the first surface of the second continuous substrate to form a continuous elastic laminate; and cutting the elastic laminate along the machine direction to form the first continuous elastic laminate and the second continuous elastic laminate.

11. The method of claim 10, wherein the graphic is located on the first surface of the first continuous substrate.

12. A method for assembling disposable diaper pants, each diaper pant comprising a chassis having a first end region and an opposing second end region separated from each other by a central region, and having a longitudinal axis and a lateral axis, the chassis comprising: a topsheet, a backsheet, and an absorbent core disposed between the topsheet and the backsheet, the method comprising the steps of:

advancing a continuous elastic laminate in a machine direction, the continuous elastic laminate having a first longitudinal edge and a second longitudinal edge defining a width, W, in a cross direction;

printing a substrate of the continuous elastic laminate to form a graphic extending in the machine direction and comprising a central zone positioned between longitudinally opposing first and second zones, wherein each zone comprises a maximum print density, wherein the maximum print density of the central zone is less than or equal to about 30% of the maximum print densities of the first and second zones, and wherein the central zone defines a length, L, in the machine direction;

cutting holes in the elastic laminate, wherein the holes spaced apart from each other along the machine direction;

depositing a plurality of chassis spaced apart from each other along the machine direction onto the continuous elastic laminate, wherein at least one hole is positioned between two consecutive chassis;

folding the continuous elastic laminate and each chassis together along the lateral axis of each chassis to position the first end region of the chassis and the opposing second end region of the chassis into a facing relationship; and cutting the continuous elastic laminate in the cross direction through the central zone of the graphic and into discrete pieces having a pitch length, PL, extending in the machine direction, wherein the pitch length PL is about 10 or more times the length L of the central zone.

13. The method of claim 12, wherein the PL is 300 mm to about 1000 mm.

14. The method of claim 12, wherein the maximum print density of the central zone is about 0.15.

15. The method of claim 12, wherein step of cutting holes is performed before the step of depositing the chassis.

16. The method of claim 12, wherein each central zone extends from the first longitudinal edge of the elastic laminate to a closest respective hole in the cross direction.

17. The method of claim 12, further comprising the step of bonding the continuous elastic laminate at pairs of discrete bond regions separated from each other along the machine direction, wherein the pairs of discrete bond regions are positioned in the central zones.

* * * * *